(12) United States Patent
Gao et al.

(10) Patent No.: US 11,819,427 B2
(45) Date of Patent: Nov. 21, 2023

(54) SYSTEMS AND METHODS FOR ORTHOSIS DESIGN

(71) Applicant: WUHAN UNITED IMAGING HEALTHCARE CO., LTD., Hubei (CN)

(72) Inventors: Jing Gao, Wuhan (CN); Qiang Shen, Wuhan (CN); Chao Tang, Wuhan (CN); Yinglong Wang, Wuhan (CN); Guodong Xie, Wuhan (CN); Mingwu Gan, Wuhan (CN); Yang Huang, Wuhan (CN); Chao Xia, Wuhan (CN); Jie Tan, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 0 days.

(21) Appl. No.: 18/157,787

(22) Filed: Jan. 20, 2023

(65) Prior Publication Data

US 2023/0157846 A1    May 25, 2023

Related U.S. Application Data

(63) Continuation of application No. 16/829,208, filed on Mar. 25, 2020, now Pat. No. 11,576,794.

(30) Foreign Application Priority Data

Jul. 2, 2019  (CN) .......................... 201910590669.3
Dec. 23, 2019  (CN) .......................... 201911342643.3
(Continued)

(51) Int. Cl.
*A61F 2/50* (2006.01)
*G06T 7/11* (2017.01)
(Continued)

(52) U.S. Cl.
CPC .......... *A61F 2/5046* (2013.01); *G06T 3/4007* (2013.01); *G06T 7/0014* (2013.01);
(Continued)

(58) Field of Classification Search
None
See application file for complete search history.

(56) References Cited

U.S. PATENT DOCUMENTS 10,052,217 B2 * 8/2018 Pallari .................. A43B 13/183
10,553,130 B2 * 2/2020 Poniatowski ......... G06T 7/0014
(Continued)

FOREIGN PATENT DOCUMENTS

CN     105250062 A     1/2016
CN     105260542 A     1/2016
(Continued)

OTHER PUBLICATIONS

First Office Action in Chinese Application No. 201911342643.3 dated Jun. 21, 2021, 27 pages.
(Continued)

*Primary Examiner* — Anand P Bhatnagar
(74) *Attorney, Agent, or Firm* — METIS IP LLC

(57) ABSTRACT

The present disclosure is related to systems and methods for orthosis design. The method includes obtaining a three-dimensional (3D) model associated with a subject. The method includes obtaining one or more reference images associated with the subject. The method includes determining, based on the 3D model and the one or more reference images, orthosis design data for the subject. The orthosis design data may be used to determine an orthosis for the subject.

20 Claims, 24 Drawing Sheets

(30) Foreign Application Priority Data

Dec. 27, 2019 (CN) .......................... 201911375163.7
Mar. 3, 2020 (CN) .......................... 202010140173.9

(51) Int. Cl.
   *G06T 7/00* (2017.01)
   *G06T 17/20* (2006.01)
   *G06T 3/40* (2006.01)

(52) U.S. Cl.
   CPC .............. *G06T 7/11* (2017.01); *G06T 17/205* (2013.01); *A61F 2002/5049* (2013.01); *G06T 2207/10076* (2013.01); *G06T 2207/10124* (2013.01); *G06T 2207/30004* (2013.01)

(56) References Cited

U.S. PATENT DOCUMENTS

| | | | |
|---|---|---|---|
| 10,564,628 B2* | 2/2020 | Hargovan | G06T 19/20 |
| 10,740,857 B2* | 8/2020 | Tuttle | H04N 13/275 |
| 11,055,887 B2* | 7/2021 | Jia | G06V 40/10 |
| 11,058,557 B2 | 7/2021 | Tompkins | |
| 11,612,506 B2* | 3/2023 | Johnson | A61H 3/008 602/16 |
| 2007/0133850 A1* | 6/2007 | Paez | G06T 7/60 382/128 |
| 2012/0019531 A1* | 1/2012 | Sabiston | G05B 19/4099 345/419 |
| 2012/0116203 A1* | 5/2012 | Vancraen | A61F 2/30942 600/407 |
| 2013/0332128 A1 | 12/2013 | Miles et al. | |
| 2015/0314533 A1* | 11/2015 | Yu | B33Y 50/00 425/166 |
| 2017/0224520 A1* | 8/2017 | Karasahin | G06V 20/64 |
| 2017/0360578 A1* | 12/2017 | Shin | G09B 23/286 |
| 2018/0300445 A1* | 10/2018 | Schouwenburg | G06F 30/17 |
| 2019/0167450 A1* | 6/2019 | Pallari | A61F 2/7812 |
| 2019/0259219 A1 | 8/2019 | Lancelle et al. | |
| 2019/0355147 A1 | 11/2019 | Li | |
| 2019/0362543 A1* | 11/2019 | Zeng | G06F 30/00 |
| 2020/0129237 A1* | 4/2020 | Ay | A61B 5/103 |
| 2020/0234870 A1* | 7/2020 | Aoki | H01F 1/18 |
| 2020/0281798 A1* | 9/2020 | Hepp | A61F 2/583 |
| 2021/0069984 A1* | 3/2021 | Opitz | A61F 2/5046 |
| 2021/0205110 A1* | 7/2021 | Johnson | A61F 5/0125 |
| 2022/0004744 A1 | 1/2022 | Xiang et al. | |

FOREIGN PATENT DOCUMENTS

| | | |
|---|---|---|
| CN | 105963005 A | 9/2016 |
| CN | 106214302 A | 12/2016 |
| CN | 106214307 A | 12/2016 |
| CN | 107943452 A | 4/2018 |
| CN | 108711194 A | 10/2018 |
| CN | 109887077 A | 6/2019 |
| CN | 110363854 A | 10/2019 |
| EP | 1576939 A1 | 9/2005 |
| KR | 20180069547 A | 6/2018 |

OTHER PUBLICATIONS

First Office Action in Chinese Application No. 202010140173.9 dated Jan. 18, 2022, 11 pages.

The Second Office Action in Chinese Application No. 201911342643.3 dated Feb. 18, 2022, 26 pages.

Chen, ZE, Research and Realization on the Approach to 3D Model Segmentation, China Master's Thesis Full-text Database Information Technology Series, 2009, 56 pages.

Yuan, Qing, The Automatic Generation Method of 3D Object's Cross-Section Drawn Based on Projecting Plane, China Master's Thesis Full-text Database Information Technology Series, 2014, 54 pages.

* cited by examiner

500

510
Obtaining a three-dimensional (3D) model associated with a subject

520
Obtaining one or more reference images associated with the subject

530
Determining, based on the 3D model and the one or more reference images, orthosis design data for the subject

| Determining, based on a 3D model and orthosis design data, force data of at least one region of a subject after wearing an orthosis | 710 |

↓

| Altering, based on the force data of the at least one region of the subject, the orthosis design data | 720 |

| Edit Patient | | | 2301 | ✕ |

Name | ID | Gender ▽

Age | Exam Date ▽ | Scan Date ▽

Height (cm) | Weight (kg)

Data

Edit Patient | Type | Filed Size | Filed State

2302

2303

[ Back ] [ Load In ]

FIG. 23

SYSTEMS AND METHODS FOR ORTHOSIS DESIGN

CROSS-REFERENCE TO RELATED APPLICATIONS

This application is a continuation of U.S. application Ser. No. 16/829,208, filed on Mar. 25, 2020, which claims priority of Chinese Patent Application No. 201911375163.7, filed on Dec. 27, 2019, Chinese Patent Application No. 201910590669.3, filed on Jul. 2, 2019, Chinese Patent Application No. 202010140173.9, filed on Mar. 3, 2020, and Chinese Patent Application No. 201911342643.3, filed on Dec. 23, 2019, the contents of each of which are hereby incorporated by reference.

TECHNICAL FIELD

The present disclosure generally relates to medical devices, and in particular, to systems and methods for orthosis design.

BACKGROUND

Orthoses are externally applied devices for modifying or correcting the structural and functional characteristics of the neuromuscular and skeletal systems. These devices are widely used for subjects (e.g., a person or an animal) having a fracture, a dislocation, or a physical deformity of the spine (e.g., scoliosis). A three-dimensional (3D) orthosis model for a subject can be designed based on image data of the subject, and an orthosis may be manufactured (e.g., by 3D printing) based on the 3D orthosis model to meet correction needs of the subject. Thus, it is desirable to design precisely accurate 3D orthosis models for subjects.

During an orthosis design process, sometimes a 3D orthosis model needs to be edited (e.g., split) to generate a desired shape. For example, a 3D orthosis model can be split according to split curve having a smooth boundary to generate a 3D orthosis sub-model having a smooth shape. However, existing model splitting algorithms often produces a rough boundary (e.g., a sawtooth boundary), reducing the quality of the 3D orthosis model. Thus, it is desirable to provide systems and methods for splitting an orthosis model smoothly.

During the orthosis design process, a large amount of data (e.g., orthosis design data) is generated. It would be crucial, therefore, to store and transfer such data so that users can access and analyze the data timely and efficiently. In addition, in some cases, a number of users (e.g., a doctor, an orthosis designer, a 3D print manufacturer) need to design and/or print an orthosis for a subject collaboratively. However, the existing orthosis design systems are often based on a client/server (C/S) architecture, which only supports local storage, resulting in reduced efficiency for multi-user collaborative design and docking with a third-party 3D print manufacturer. Furthermore, the existing orthosis design systems often do not have a cross-platform and rapid deployment function, leading to low response speed and instability in a high concurrency environment. Therefore, it is desirable to provide effective systems and methods for orthosis design.

SUMMARY

According to an aspect of the present disclosure, a method for orthosis design may be implemented on a computing device having one or more processors and one or more storage devices. The method may include obtaining a three-dimensional (3D) model associated with a subject. The method may include obtaining one or more reference images associated with the subject. The method may include determining, based on the 3D model and the one or more reference images, orthosis design data for the subject. The orthosis design data may be used to determine an orthosis for the subject.

In some embodiments, the method may include obtaining the 3D model associated with the subject from a 3D camera device.

In some embodiments, the method may include obtaining image data associated with the subject. The method may include determining the 3D model associated with the subject based on the image data associated with the subject.

In some embodiments, the method may include determining a target area by performing an image segmentation operation on the image data associated with the subject. The method may include extracting body surface data associated with the target area from the image data associated with the subject. The method may include generating a plurality of meshes of the 3D model based on the body surface data associated with the target area.

In some embodiments, the one or more reference images may be digital radiography (DR) images.

In some embodiments, the method may include comparing the 3D model with the one or more reference images. The method may include determining the orthosis design data by modifying the 3D model based on a comparison result.

In some embodiments, the orthosis design data for the subject may include a processing result determined by performing at least one of a mesh deformation operation, a mesh smoothing operation, a mesh division operation, or a mesh splitting operation on the 3D model.

In some embodiments, the method may include determining, based on the 3D model and the orthosis design data, force data of at least one region of the subject after wearing an orthosis. The method may include altering, based on the force data of the at least one region of the subject, the orthosis design data.

In some embodiments, the method may include determining housing design data associated with a housing of the orthosis by performing a thickness-adjustment operation on the orthosis design data.

According to another aspect of the present disclosure, a method for splitting a 3D model may be implemented on a computing device having one or more processors and one or more storage devices. The method may include determining a spline curve associated with a 3D model. The spline curve may be generated based on a plurality of first coordinates input by a user in a screen coordinate system. The spline curve may include a plurality of second coordinates in a model coordinate system. For each second coordinate of the plurality of second coordinates, the method may include determining a center point corresponding to the second coordinate. The method may include determining a link line connecting the center point and the corresponding second coordinate. The method may include determining a plurality of boundary points along a direction of the link line. The method may include generating a split surface based on all the boundary points corresponding to the plurality of second coordinates.

In some embodiments, the method may include splitting the 3D model based on the split surface.

In some embodiments, the method may include obtaining the plurality of first coordinates input by the user. The method may include determining a plurality of third coordinates by performing a spline interpolation operation on the plurality of first coordinates. The method may include determining the plurality of second coordinates by projecting the plurality of third coordinates on the 3D model. The method may include determining the spline curve by connecting the plurality of second coordinates.

In some embodiments, the spline interpolation operation may include at least one of a cubic B-spline interpolation, a Bezier curve interpolation, or a catmull-rom curve interpolation.

In some embodiments, the plurality of boundary points may include an inner boundary point and an outer boundary point. The inner boundary point may be located inside the 3D model. The outer boundary point may be located outside the 3D model. For the each second coordinate of the plurality of second coordinates, the method may include determining the inner boundary point by extending the second coordinate to the inside of the 3D model along the direction of the link line. The method may include determining the outer boundary point by extending the second coordinate to the outside of the 3D model along the direction of the link line.

In some embodiments, the method may include generating a plurality of split sub-surfaces by connecting the inner boundary points and the outer boundary points corresponding to the plurality of second coordinates. The method may include generating the split surface by combining the plurality of split sub-surfaces.

In some embodiments, the method may include transforming the plurality of third coordinates in the screen coordinate system to a plurality of fourth coordinates in a view coordinate system. The method may include transforming the plurality of fourth coordinates in the view coordinate system to a plurality of fifth coordinates in a camera coordinate system. The method may include transforming the plurality of fifth coordinates in the camera coordinate system to a plurality of sixth coordinates in a world coordinate system. The method may include transforming the plurality of sixth coordinates in the world coordinate system to the plurality of second coordinates in the model coordinate system.

In some embodiments, prior to obtaining the plurality of first coordinates, the method may include obtaining data associated with the 3D model. The method may include determining an initial transformation matrix between the model coordinate system and the world coordinate system. The initial transformation matrix may be used to display a front view of the 3D model in the world coordinate system. The method may include rendering the 3D model based on the data associated with the 3D model and the initial transformation matrix.

In some embodiments, the method may include generating at least two sub-models by splitting the 3D model based on the split surface. The method may include displaying the at least two sub-models on a terminal device associated with the user.

According to another aspect of the present disclosure, a system for orthosis design may include at least one storage device storing a set of instructions, and at least one processor in communication with the at least one storage device. When executing the stored set of instructions, the at least one processor may cause the system to obtain a three-dimensional (3D) model associated with a subject. The at least one processor may cause the system to obtain one or more reference images associated with the subject. The at least one processor may cause the system to determine, based on the 3D model and the one or more reference images, orthosis design data for the subject. The orthosis design data may be used to determine an orthosis for the subject.

In some embodiments, the at least one processor may cause the system to obtain the 3D model associated with the subject from a 3D camera device.

In some embodiments, the at least one processor may cause the system to determine the 3D model associated with the subject based on the image data associated with the subject.

In some embodiments, the at least one processor may cause the system to determine a target area by performing an image segmentation operation on the image data associated with the subject. The at least one processor may cause the system to extract body surface data associated with the target area from the image data associated with the subject. The at least one processor may cause the system to generate a plurality of meshes of the 3D model based on the body surface data associated with the target area.

In some embodiments, the at least one processor may cause the system to compare the 3D model with the one or more reference images. The at least one processor may cause the system to determine the orthosis design data by modifying the 3D model based on a comparison result.

In some embodiments, the at least one processor may cause the system to determine, based on the 3D model and the orthosis design data, force data of at least one region of the subject after wearing an orthosis. The at least one processor may cause the system to alter, based on the force data of the at least one region of the subject, the orthosis design data.

In some embodiments, the at least one processor may cause the system to determine housing design data associated with a housing of the orthosis by performing a thickness-adjustment operation on the orthosis design data.

In some embodiments, the system may include at least one data obtaining device configured to obtain data associated with the subject. The data associated with the subject may include at least one of the image data associated with the subject, the 3D model associated with the subject, or one or more reference images associated with the subject.

In some embodiments, the system may include at least one first terminal device configured to import the data associated with the subject.

In some embodiments, the system may include the at least one second terminal device configured to send a request for orthosis design.

In some embodiments, the at least one processor may include a plurality of processing devices. The system may include a data interaction equipment, configured to transmit the request for orthosis design obtained from the at least one second terminal device to at least one processing device of the plurality of processing devices, according to a load balancing mechanism.

In some embodiments, the data interaction equipment may include a first load balancing device, a data interaction device cluster including a plurality of data interaction devices, and a second load balancing device. The first load balancing device may communicate with the at least one first terminal device and the at least one second terminal device, and may be configured to transmit data from the at least one first terminal device and the at least one second terminal device to at least one data interaction device of the data interaction device cluster according to the load balancing mechanism. The at least one data interaction device may be configured to determine the request for orthosis design based on the data obtained from the at least one first terminal device and the at least one second terminal device. The second load balancing device may communicate with the data interaction device cluster, and may be configured to transmit the request for orthosis design to the at least one data processing device of the data processing device cluster, according to the load balancing mechanism In some embodiments, the at least one first terminal device and the at least one second terminal device may communicate with the data interaction device via a browser.

In some embodiments, the system may be based on ASP.NET Core technology.

In some embodiments, the data interaction equipment may be a reverse proxy.

In some embodiments, the at least one second terminal device may include a plurality of second terminal devices associated with a plurality of users. The plurality of second terminal devices may be configured to send a plurality of requests for determining the orthosis cooperatively.

In some embodiments, the system may include a 3D print device configured to print the orthosis based on the orthosis design data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5 is a flowchart illustrating an exemplary process for designing an orthosis according to some embodiments of the present disclosure;

FIG. 7 is a flowchart illustrating an exemplary process for altering orthosis design data according to some embodiments of the present disclosure;

FIG. 23 is a schematic diagram illustrating an exemplary user interface for displaying a patient list according to some embodiments of the present disclosure.

DETAILED DESCRIPTION

Figure 1:
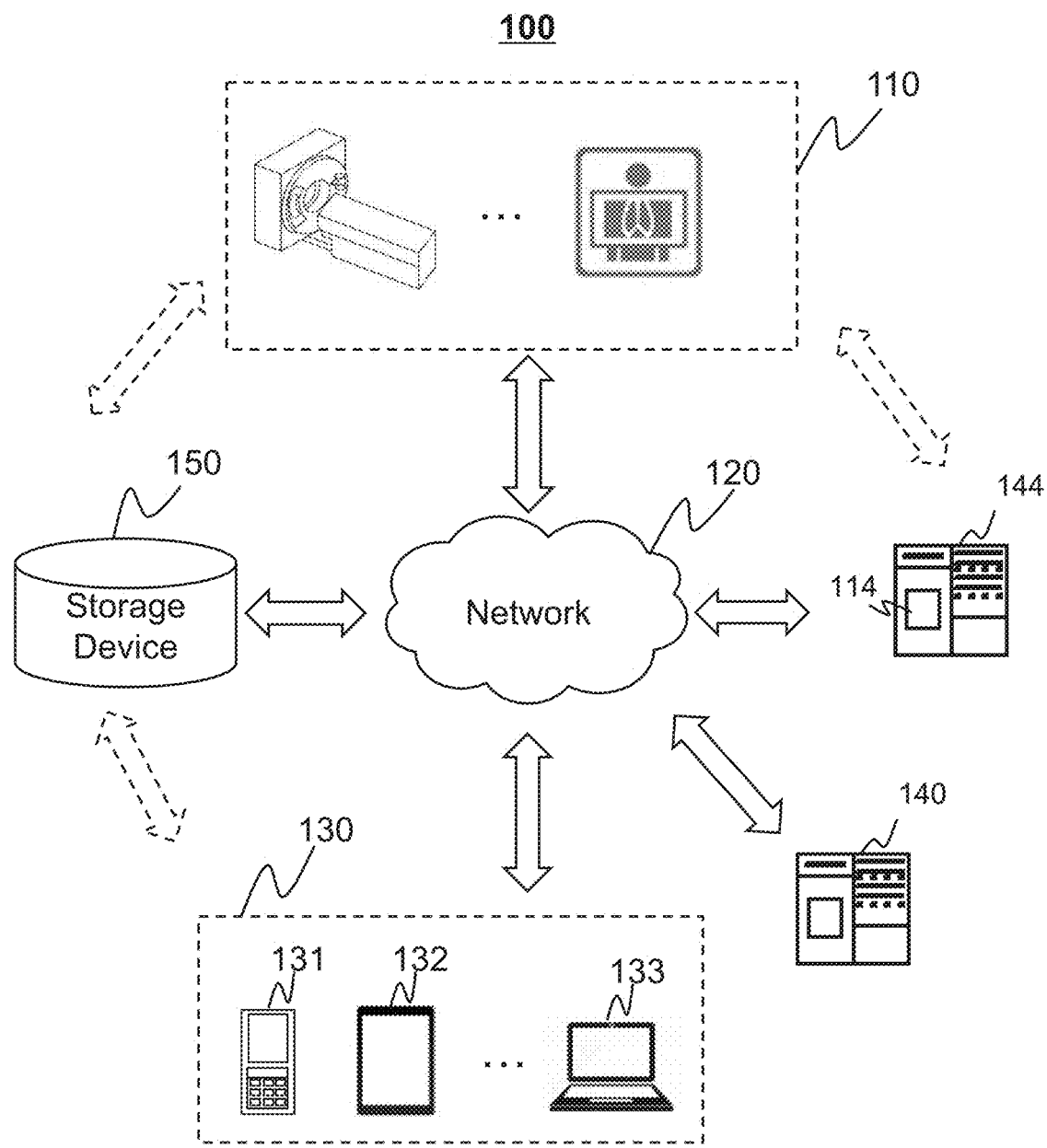
FIG. 1 is a schematic diagram illustrating an exemplary orthosis design system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operations and functions of the related elements of structure and the combination of parts and economies of manufacture, may become more apparent upon consideration of the following description with reference to the accompanying drawing(s), all of which form part of this specification. It is to be expressly understood, however, that the drawing(s) is for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in an inverted order, or simultaneously. Moreover, one or more other operations may be added to the flowcharts. One or more operations may be removed from the flowcharts.

An aspect of the present disclosure relates to methods and systems for orthosis design. According to some embodiments of the present disclosure, a processing device may obtain a three-dimensional (3D) model associated with a subject. The processing device may obtain one or more reference images (e.g., a digital radiography image) associated with the subject. The processing device may determine, based on the 3D model and the one or more reference images, orthosis design data for the subject. The orthosis design data may be used to determine an orthosis for the subject. In some embodiments, the processing device may compare the 3D model with the one or more reference images. The processing device may determine the orthosis design data by modifying (e.g., splitting) the 3D model based on a comparison result. Accordingly, orthosis design data for a subject may be generated based on one or more reference images of the subject and a 3D model of the subject. An orthosis generated based on the orthosis design data may meet correction needs of the subject.

Another aspect of the present disclosure relates to methods and systems for splitting a 3D model. The processing device may determine a spline curve associated with a 3D model. The spline curve may be generated based on a plurality of first coordinates input by a user in a screen coordinate system. The spline curve may include a plurality of second coordinates in a model coordinate system. For each second coordinate of the plurality of second coordinates, the processing device may determine a center point corresponding to the second coordinate. The processing device may determine a link line connecting the center point and the corresponding second coordinate. The processing device may determine a plurality of boundary points along a direction of the link line. The processing device may generate a split surface based on all the boundary points corresponding to the plurality of second coordinates.

Accordingly, a method for determining a split surface based on a plurality of dynamic center points may be provided. The problems of split surface self-intersections and a non-smoothing boundary of the split surface caused by an irregular body surface of the 3D model may be avoided.

Another aspect of the present disclosure related to methods and systems for data management in an orthosis design system. The data management system may include an importing module, a storage module, and a printing module. The importing module (e.g., a terminal device associated with a doctor) may import data associated with a subject. The storage module (e.g., a terminal device associated with an orthosis designer) may store data associated with an orthosis during an orthosis design process. The printing module (e.g., a terminal device associated with a 3D print manufacturer) may print the orthosis based on the data associated with the subject and/or the data associated with the orthosis. Accordingly, a plurality of users (e.g., a doctor, an orthosis designer, a 3D print manufacturer) of the orthosis design system 100 may design and/or print an orthosis for a subject via a plurality of browsers on a plurality of terminal devices collaboratively. The orthosis design and print process may be simplified, and the orthosis production efficiency may be improved.

FIG. 1 is a schematic diagram illustrating an exemplary orthosis design system 100 according to some embodiments of the present disclosure. The orthosis design system 100 may include a data obtaining device 110, a network 120, at least one terminal device 130, a server 144, a data interaction equipment 140, and a storage device 150. The server 144 and the data interaction equipment 140 may also be referred to as a cloud design system. The components of the orthosis design system 100 may be connected in one or more of various ways. Merely by way of example, as illustrated in FIG. 1, the data obtaining device 110 may be connected to the storage device 150 directly as indicated by the bi-directional arrow in dotted lines linking the data obtaining device 110 and the storage device 150, or through the network 120. As another example, the terminal device 130 may be connected to the storage device 150 directly as indicated by the bi-directional arrow in dotted lines linking the terminal device 130 and the storage device 150, or through the network 120. As another example, the server 144 may be connected to the data obtaining device 110 directly as indicated by the bi-directional arrow in dotted lines linking the server 144 and data obtaining device 110, or through the network 120. As still another example, the at least one terminal device 130 may be connected to the server 144 via the network 120.

The data obtaining device 110 may be configured to acquire image data relating to at least one part of a subject. The image data relating to at least one part of a subject may include an image (e.g., an image slice), projection data, or a combination thereof. For example, the data obtaining device 110 may scan a portion of the subject to be corrected to obtain scanned image data or a 3D model of the portion of the subject to be corrected. In some embodiments, the image data may be a two-dimensional (2D) imaging data, a three-dimensional (3D) imaging data, a four-dimensional (4D) imaging data, or the like, or any combination thereof. In some embodiments, the image data may include a magnetic resonance imaging (MRI) image, a computerized tomography (CT) image, a direct digital X-ray photography image, a computer X-ray image, or the like, or any combination thereof.

The subject may be biological or non-biological. In some embodiments, the subject may include a patient, a man-made object, etc. In some embodiments, the subject may include a specific portion, an organ, and/or tissue of the patient. For example, the subject may include the head, the neck, the thorax, the heart, the stomach, a blood vessel, soft tissue, a tumor, nodules, or the like, or any combination thereof.

In some embodiments, the data obtaining device 110 may include a single modality imaging device. For example, the data obtaining device 110 may include a positron emission tomography (PET) device, a single-photon emission computed tomography (SPECT) device, a magnetic resonance imaging (MRI) device, a computed tomography (CT) device, an ultrasound (US) device, a X-ray imaging device (e.g., a suspended X-ray imaging device, a digital radiography (DR) scanner), or the like, or any combination thereof. In some embodiments, the data obtaining device 110 may include a multi-modality imaging device. Exemplary multi-modality imaging devices may include a PET-CT device, a PET-MRI device, or the like, or a combination thereof.

In some embodiments, the data obtaining device 110 may be a 3D camera (e.g., a 3D scanner). The 3D camera may obtain a 3D model of the subject. In some embodiments, the data obtaining device 110 may be configured to acquire one or more reference images of the subject. In some embodiments, the reference image may include a 2D digital radiography image (e.g., a DR plain film).

The network 120 may include any suitable network that can facilitate the exchange of information and/or data for the orthosis design system 100. In some embodiments, one or more components of the orthosis design system 100 (e.g., the data obtaining device 110, the at least one terminal device 130, the server 144, the data interaction equipment 140, the storage device 150, etc.) may communicate information and/or data with one or more other components of the orthosis design system 100 via the network 120. For example, the processing device 114 may obtain image data (e.g., one or more reference images) and/or a 3D model of a subject from the data obtaining device via the network 120. As another example, the processing device 114 may obtain user instruction(s) from the terminal device 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the orthosis design system 100 may be connected to the network 120 to exchange data and/or information.

The terminal device 130 may communicate and/or connect with the data obtaining device 110, the server 144, the data interaction equipment 140, and/or the storage device 150. For example, at least one terminal device 130 may obtain orthosis design data from the server 144 for design an orthosis. As another example, the at least one terminal device 130 may obtain image data acquired by the data obtaining device 110, and send the image data to the data interaction equipment 140 and the server 144 for processing. In some embodiments, the at least one terminal device 130 may include a mobile device 131, a tablet computer 132, a laptop computer 133, or the like, or any combination thereof. For example, the mobile device 131 may include a mobile phone, a personal digital assistant (PDA), a gaming device, a navigation device, or the like, or any combination thereof. In some embodiments, the at least one terminal device 130 may include an input device, an output device, or the like. The input devices may include alphanumeric and other keys. The input device may use keyboard input, touch screen (for example, with tactile or haptic feedback) input, voice input, eye tracking input, brain monitoring system input, or any other similar input mechanism. The input information received through the input device may be transmitted to the cloud design system via a bus for further processing. Other types of input devices may include cursor control devices, such as a mouse, a trajectory ball, or a cursor direction key. The output device may include a display, a speaker, a printer, etc. or any combination thereof. In some embodiments, the at least one terminal device 130 may be portion of the cloud design system. In some embodiments, the terminal device 130 may communicate with the data interaction equipment 140 and/or the server 144 via a browser.

In some embodiments, the terminal device 130 may include one or more first terminal devices and one or more second terminal devices. The first terminal device may be associated with a first type of user in the orthosis design system 100. For example, the first terminal device may be associated with a doctor. The doctor may import data associated with the subject to one or more storage device (e.g., the storage device 150) of the orthosis design system via the first terminal device. The data associated with the subject may include identification information of the subject (e.g., an identification (ID) number of the subject, a name of the subject, the gender of the subject, the age of the subject, a portion of the subject to be corrected), image data associated with the subject, a 3D model associated with the subject, a reference image associated with the subject, or the like, or any combination thereof. The second terminal device may be associated with a second type of user in the orthosis design system 100. For example, the second terminal device may be associated with an orthosis designer. The orthosis designer may send a request for orthosis design via the second terminal device. In some embodiments, a plurality of users associated with the plurality of terminal devices 130 may send a plurality of requests for determining an orthosis collaboratively. For example, a first terminal device associated with a first user is located in a first location. A second terminal device associated with a second user is located in a second location. The first location may be different from the second location. The first user and the second user may send requests for designing an orthosis to the data interaction equipment 140 synchronously.

Figure 21:
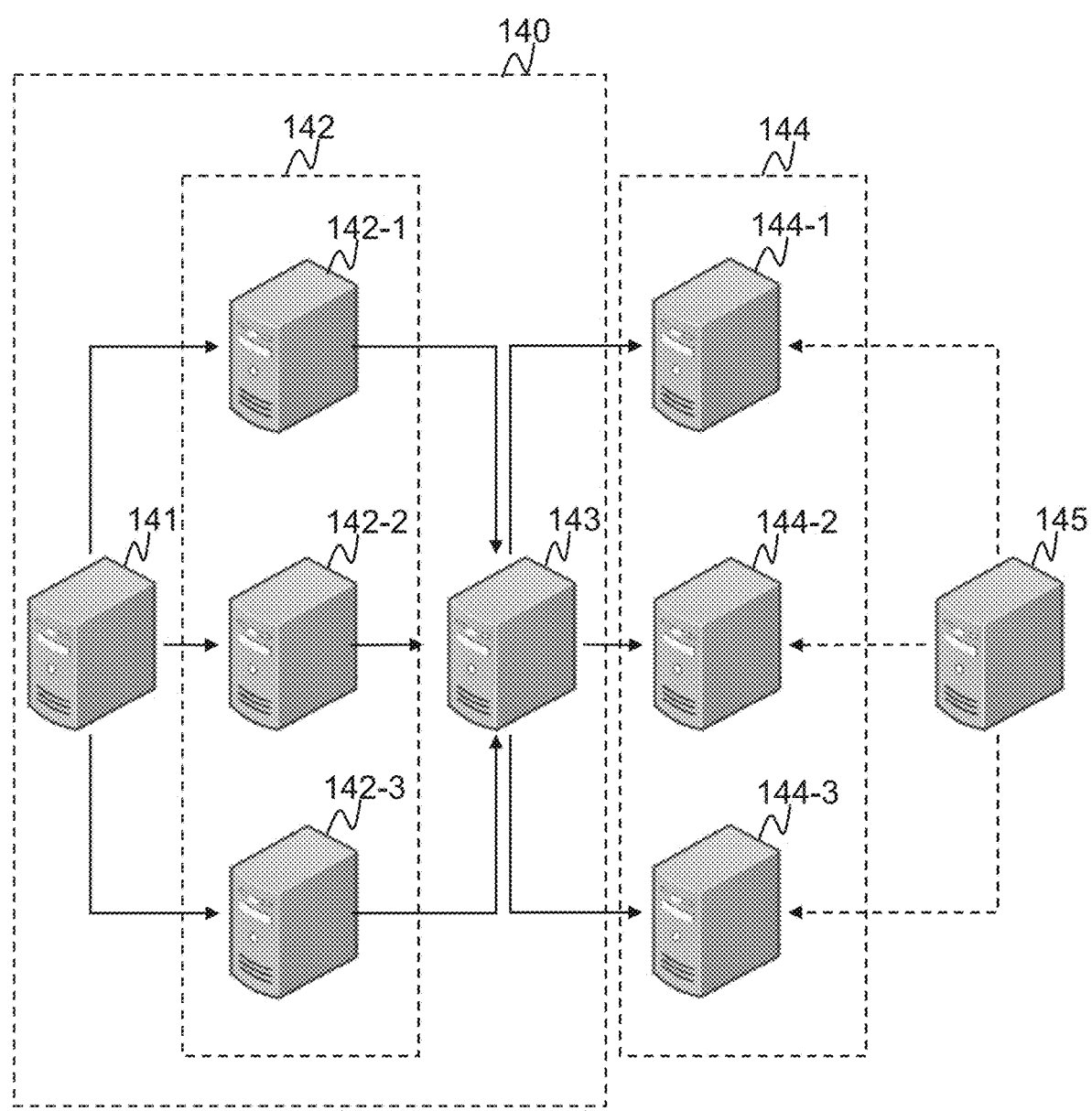
FIG. 21 is a schematic diagram illustrating an exemplary cloud design system according to some embodiments of the present disclosure.

In some embodiments, the server 144 may be a single server or a server group. The server group may be centralized or distributed (e.g., the server 144 may be a distributed system). For example, the server 144 may include a plurality of servers, e.g., a server 144-1, a server 144-2, a server 144-4, as illustrated in FIG. 21. In some embodiments, the server 144 may be local or remote. For example, the server 144 may access information and/or data stored in the terminal device 130, the storage device 150, the data obtaining device 110 via the network 120. As another example, the server 144 may be directly connected to the terminal device 130, the storage device 150, the data obtaining device 110 to access stored information and/or data. In some embodiments, the server 144 may be implemented on a cloud platform or an onboard computer. Merely by way of example, the cloud platform may include a private cloud, a public cloud, a hybrid cloud, a community cloud, a distributed cloud, an inter-cloud, a multi-cloud, or the like, or any combination thereof. In some embodiments, the server 144 may be implemented on a computing device 200 having one or more components illustrated in FIG. 2 in the present disclosure.

In some embodiments, the server 144 may include a processing device 114.

The processing device 114 may process information and/or data to perform one or more functions described in the present disclosure. For example, the processing device 114 may obtain a 3D model associated with a subject. As another example, the processing device 114 may obtain one or more reference images associated with a subject. As still another example, the processing device 114 may determine, based on a 3D model and one or more reference images, orthosis design data for a subject. As still another example, the processing device 114 may edit (e.g., split) a 3D model. As still another example, the processing device 114 may initialize a 3D model. As still another example, the processing device 114 may determine a spline curve associated with a 3D model. As still another example, for each second coordinate of a plurality of second coordinates on a spline curve, the processing device 114 may determine a center point corresponding to the second coordinate. As still another example, the processing device 114 may determine a link line connecting a center point and a corresponding second coordinate. As still another example, the processing device 114 may determine a plurality of boundary points along a direction of a link line. As still another example, the processing device 114 may generate a split surface based on all boundary points corresponding to a plurality of second coordinates. As still another example, the processing device 114 may split a 3D model based on a split surface.

In some embodiments, the processing device 114 may include one or more processing engines (e.g., single-core processing engine(s) or multi-core processor(s)). Merely by way of example, the processing device 114 may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a controller, a microcontroller unit, a reduced instruction-set computer (RISC), a microprocessor, or the like, or any combination thereof.

In some embodiments, the server 144 may be connected to the network 120 to communicate with one or more components (e.g., the terminal device 130, the storage device 150, the data obtaining device 110) of the orthosis design system 100. In some embodiments, the server 144 may be directly connected to or communicate with one or more components (e.g., the terminal device 130, the storage device 150, and/or the data obtaining device 110) of the orthosis design system 100.

The data interaction equipment 140 may be configured to transmit data obtained from the terminal device 130 to the server 144. In some embodiments, the data interaction equipment 140 may transmit one or more requests for orthosis design obtained from one or more terminal devices 130 to one or more servers according to a load balancing mechanism. In some embodiments, the data interaction equipment 140 may include a first load balancing device, a data interaction device cluster including a plurality of data interaction devices, and a second load balancing device. More descriptions of the data interaction equipment 140 may be found elsewhere in the present disclosure (e.g., FIG. 21 and descriptions thereof).

In some embodiments, the data interaction equipment 140 may be a reverse proxy. As used herein, a reverse proxy may refer to a type of proxy server that retrieves resources on behalf of a client from one or more servers. These resources are then returned to the client, appearing as if they originated from the proxy server itself. In some embodiments, the reverse proxy may include a nginx, a haproxy, or the like. More descriptions of the proxy server may be found elsewhere in the present disclosure (e.g., FIG. 22 and descriptions thereof).

The storage device 150 may store data, instructions, and/or any other information. In some embodiments, the storage device 150 may store data obtained from the data obtaining device 110, the terminal device 130, the processing device 114. In some embodiments, the storage device 150 may store data and/or instructions that the processing device 114 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components in the orthosis design system 100 (e.g., the terminal device 130, the server 144, the data obtaining device 110). At least one component in the orthosis design system 100 may access data or instructions stored in the storage device 150 through the network 120. In some embodiments, the storage device 150 may be portion of the cloud design system.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure.

In some embodiments, the orthosis design system 100 may be based on a browser/server (B/S) architecture. The B/S architecture may run an application directly from an internet browser on any device that has a browser (e.g., a laptop, a tablet, a smartphone). For example, a browser may be installed on the terminal device 130. The user of the terminal device 130 may communicate with the server 144 via the browser. In some embodiments, a plurality of main functions of the orthosis design system 100 may be implemented on the server 144. For example, the server 144 may determine orthosis design data for a subject. As still another example, the sever 144 may edit (e.g., split) a 3D model. In some embodiments, a plurality of relatively simple functions of the orthosis design system 100 may be implemented on the terminal device 130. For example, the terminal device 130 may obtain data associated with a subject (e.g., a 3D model of the subject, a reference image of the subject). Accordingly, a computing load of the terminal device 130 may be reduced. The maintenance and upgrade cost of the orthosis design system 100 may be reduced. The total cost of a user of the orthosis design system 100 may further be reduced.

In some embodiments, the orthosis design system 100 may be based on ASP.NET Core technology. As used herein, ASP.NET Core may refer to a cross-platform, high-performance, open-source framework for building modern, cloud-based, internet-connected applications. In some embodiments, the orthosis design system 100 may be developed on Windows, macOS, and/or Linux. In some embodiments, the orthosis design system 100 may be deployed to cloud or on-premises. In some embodiments, the orthosis design system 100 may be hosted in internet information services (IIS), nginx, apache, docker, or the like. Accordingly, a cross-platform orthosis design system 100 may be developed.

In some embodiments, the orthosis design system 100 may include a database. In some embodiments, the database may include a medical imaging information system. For example, the database may be a picture archiving and communication system (PACS). The PACS may refer to a medical imaging technology which provides economical storage and convenient access to images from multiple modalities (source machine types). For example, the PACS may store a plurality of images (e.g., a plurality of medical images) generated by a plurality of medical devices (e.g., a nuclear magnetic resonance (NMR), a computer tomography (CT) device, a digital X-ray (DR) device, an ultrasound device, an X-ray imaging device) in a medical imaging department of a hospital. The format for PACS image storage and transfer may be digital imaging and communications in medicine (DICOM).

In some embodiments, the orthosis design system 100 may include a 3D printing server. The 3D printing server may be connected to a 3D printing device to print an orthosis based on housing design data, orthosis design data, and/or a plurality of 3D printing parameters associated with the orthosis as described elsewhere in the present disclosure.

Figure 17:
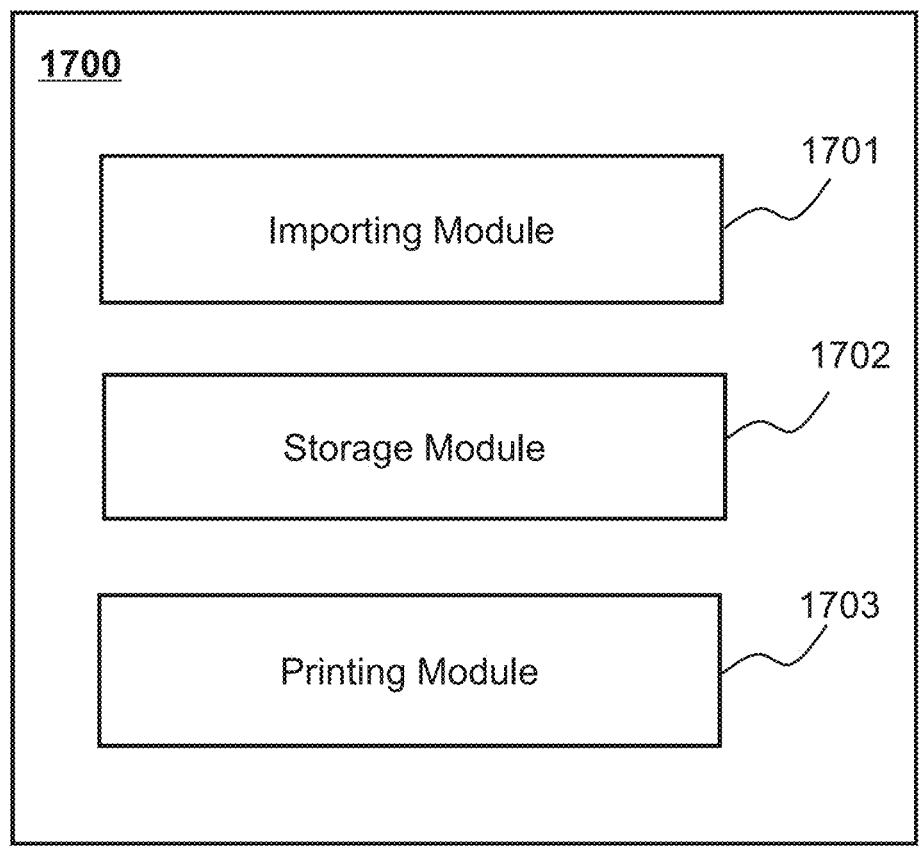
FIG. 17 is a block diagram illustrating an exemplary data management system according to some embodiments of the present disclosure.

In some embodiments, the orthosis design system 100 may include a data management system (e.g., a data management system 1700 as illustrated in FIG. 17). The data management system may be configured to manage data associated with the orthosis design system 100. The data associated with the orthosis design system 100 may include identification information of the subject (e.g., an identification (ID) number of the subject, a name of the subject, the gender of the subject, the age of the subject, a portion of the subject to be corrected), image data of the subject, a 3D model of the subject, orthosis design data, housing design data associated with a housing of the orthosis, a 3D printing parameter of the orthosis, or the like, or any combination thereof. In some embodiments, the data management system may include an importing module (e.g., an importing module 1701 as illustrated in FIG. 17), a storage module (e.g., a storage module 1702 as illustrated in FIG. 17), and a printing module (e.g., a printing module 1703 as illustrated in FIG. 17). More descriptions of the data management system may be found elsewhere in the present disclosure (e.g., FIGS. 17, 18, 19, 20, and descriptions thereof).

Figure 2:
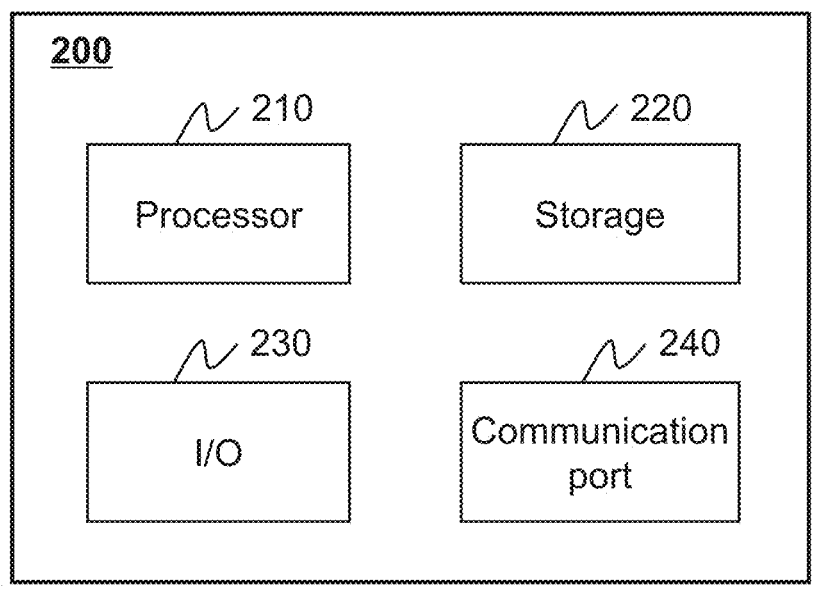
FIG. 2 is a schematic diagram illustrating hardware and/or software components of an exemplary computing device according to some embodiments of the present disclosure.

FIG. 2 is a schematic diagram illustrating hardware and/or software components of an exemplary computing device according to some embodiments of the present disclosure. As illustrated in FIG. 2, the computing device 200 may include a processor 210, a storage 220, an input/output (I/O) 230, and a communication port 240. In some embodiments, the processing device 114 and/or the terminal device 130 may be implemented on the computing device 200.

The processor 210 may execute computer instructions (program code) and, when executing the instructions, cause the processing device 114 to perform functions of the processing device 114 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the data obtaining device 110, the terminal device 130, the storage device 150, and/or any other components of the orthosis design system 100. For example, the processor 210 may obtain image data from the data obtaining device 110. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the data obtaining device 110, the terminal device 130, the storage device 150, the server 144, or any other components of the orthosis design system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program (e.g., in the form of computer-executable instructions) for the processing device 114 to determine orthosis design data. As another example, the storage 220 may store a program (e.g., in the form of computer-executable instructions) for the processing device 114 to determine a split surface of a 3D model.

The I/O 230 may input or output signals, data, and/or information. In some embodiments, the I/O 230 may enable user interaction with the processing device 114. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 160) to facilitate data communications. The communication port 240 may establish connections between the processing device 114 and the data obtaining device 110, the terminal device 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
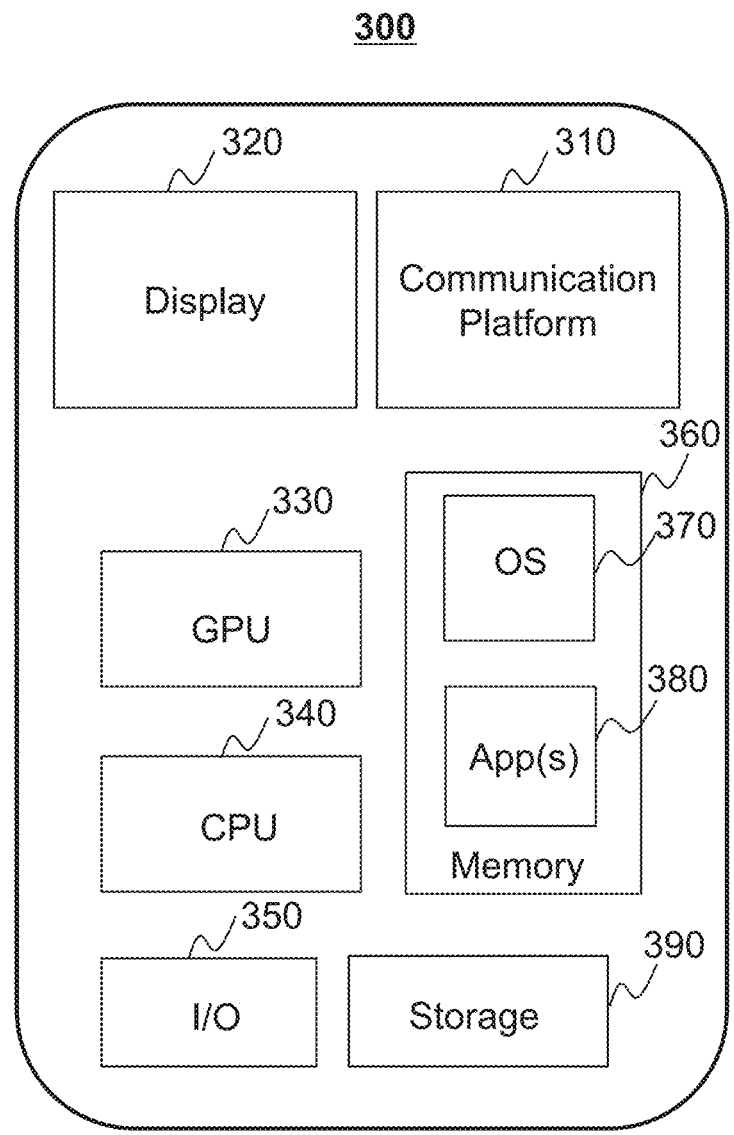
FIG. 3 is a schematic diagram illustrating hardware and/or software components of a mobile device according to some embodiments of the present disclosure.

FIG. 3 is a schematic diagram illustrating hardware and/or software components of a mobile device according to some embodiments of the present disclosure. In some embodiments, the processing device 114 and/or the terminal device 130 may be implemented on the computing device 200. As illustrated in FIG. 3, the mobile device 300 may include a communication platform 310, a display 320, a graphics processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to orthosis design or other information from the processing device 114. User interactions with the information stream may be achieved via the I/O 350 and provided to the processing device 114 and/or other components of the orthosis design system 100 via the network 120.

To implement various modules, units, and functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate a high-quality image of a scanned object as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
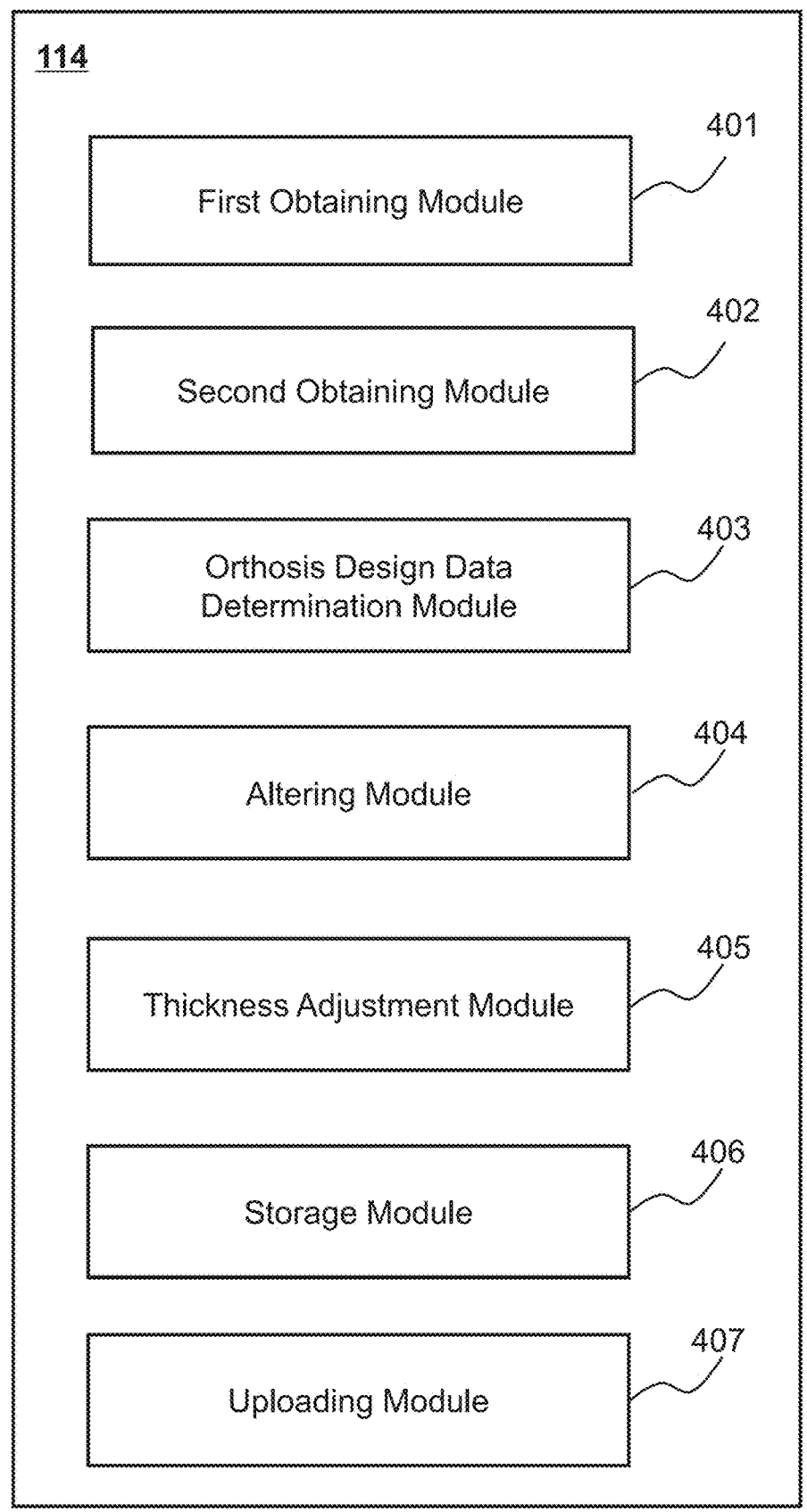
FIG. 4 is a block diagram illustrating an exemplary processing device according to some embodiments of the present disclosure.

FIG. 4 is a block diagram illustrating an exemplary processing device according to some embodiments of the present disclosure. The processing device 114 may include a first obtaining module 401, a second obtaining module 402, an orthosis design data determination module 403, an altering module 404, a thickness adjustment module 405, a storage module 406, and an uploading module 407. The modules may be hardware circuits of at least part of the processing device 114. The modules may also be implemented as an application or set of instructions read and executed by the processing device 114. Further, the modules may be any combination of the hardware circuits and the application/instructions. For example, the modules may be part of the processing device 114 when the processing device 114 is executing the application or set of instructions.

The first obtaining module 401 may be configured to obtain a 3D model associated with a subject. In some embodiments, the first obtaining module 401 may obtain a 3D model associated with a subject from a 3D camera device (e.g., a 3D scanner). In some embodiments, the first obtaining module 401 may obtain image data (e.g., a plurality of medical images) associated with a subject. The first obtaining module 401 may determine a 3D model associated with the subject by processing the image data associated with the subject. For example, the first obtaining module 401 may determine a target area by performing an image segmentation operation on the image data associated with the subject. The first obtaining module 401 may extract body surface data associated with the target area from the image data associated with the subject. The first obtaining module 401 may generate a plurality of meshes of the 3D model based on the body surface data associated with the target area. In some embodiments, the first obtaining module 401 may process body surface data. For example, the first obtaining module 401 may perform a filtering operation, a smoothing operation, a boundary calculation operation, or the like, or any combination thereof, on the body surface data. More descriptions of the obtaining of the 3D model may be found elsewhere in the present disclosure (e.g., FIGS. 5, 6, and descriptions thereof).

The second obtaining module 402 may be configured to obtain a reference image associated with a subject. In some embodiments, the second obtaining module 402 may obtain one or more reference images associated with a subject from the data obtaining device 110 (e.g., a DR device, an X-ray imaging device, a camera). In some embodiments, the second obtaining module 402 may obtain one or more reference images based on the identification information of a subject. In some embodiments, the second obtaining module 402 may obtain one or more reference images based on a machine learning model. More descriptions of the obtaining of the one or more reference images may be found elsewhere in the present disclosure (e.g., FIG. 5 and descriptions thereof).

The orthosis design data determination module 403 may be configured to determine orthosis design data for a subject. In some embodiments, the orthosis design data determination module 403 may determine orthosis design data for a subject based on a 3D model of the subject and one or more reference images of the subject. For example, the orthosis design data determination module 403 may compare a 3D model of a subject with one or more reference images of the subject. The orthosis design data determination module 403 may determine orthosis design data by modifying the 3D model based on a comparison result. More descriptions of determination of orthosis design data for a subject may be found elsewhere in the present disclosure (e.g., FIG. 5 and descriptions thereof).

The altering module 404 may be configured to alter orthosis design data. In some embodiments, the altering module 404 may determine force data of at least one region of a subject after wearing an orthosis based on a 3D model of the subject and orthosis design data for the subject. The altering module 404 may alter the orthosis design data based on the force data of the at least one region of the subject. More descriptions for altering orthosis design data for a subject may be found elsewhere in the present disclosure (e.g., FIG. 5 and descriptions thereof).

The thickness adjustment module 405 may be configured to determine housing design data associated with a housing of an orthosis. In some embodiments, the thickness adjustment module 405 may determine housing design data associated with a housing of an orthosis by performing a thickness-adjustment operation on orthosis design data. In some embodiments, the housing design data may represent a size of the orthosis. For example, the housing design data may include a length, a width, a height, a thickness of the orthosis, or the like, or any combination thereof. More descriptions of determination of the housing design data may be found elsewhere in the present disclosure (e.g., FIG. 5 and descriptions thereof).

The storage module 406 may be configured to store data and/or information associated with the orthosis design system 100. The data associated with the orthosis design system 100 may include identification information of the subject (e.g., an identification (ID) number of the subject, a name of the subject, the gender of the subject, the age of the subject, a portion of the subject to be corrected), image data of the subject, a 3D model of the subject, orthosis design data, housing design data associated with a housing of the orthosis, a 3D printing parameter of the orthosis, or the like, or any combination thereof.

The uploading module 407 may be configured to transmit data and/or information associated with the orthosis design system 100 to one or more other components of the orthosis design system 100. In some embodiments, the uploading module 407 may transmit housing design data to a server (e.g., a 3D print server) for 3D printing.

It should be noted that the above description of the processing device 114 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the first obtaining module 401 and the second obtaining module may be combined into a single module, which may both obtain a 3D model of a subject and one or more reference images of the subject. In some embodiments, one or more modules may be added or omitted in the processing device 114. For example, the storage module 406 may be omitted. Data associated with the orthosis design system 100 may be stored in one or more storage devices (e.g., the storage device 150) of the orthosis design system 100, or an external storage device. As another example, the altering module 404 may be omitted. The orthosis design data determination module 403 may alter the orthosis design data.

FIG. 5 is a flowchart illustrating an exemplary process for designing an orthosis according to some embodiments of the present disclosure. Process 500 may be executed by the orthosis design system 100. For example, process 500 may be implemented as a set of instructions (e.g., an application) stored in the storage device 150 in the orthosis design system 100. The processing device 114 may execute the set of instructions and may accordingly be directed to perform process 500 in the orthosis design system 100. The operations of the illustrated process 500 presented below are intended to be illustrative. In some embodiments, process 500 may be accomplished with one or more additional operations not described, and/or without one or more of the operations discussed. Additionally, the order in which the operations of process 500 as illustrated in FIG. 5 and described below is not intended to be limiting.

In 510, the processing device 114 (e.g., the first obtaining module 401) may obtain a 3D model associated with a subject.

The subject may be biological or non-biological. In some embodiments, the subject may include a patient, an animal, a man-made object, etc. In some embodiments, the subject may include a specific portion, organ, and/or tissue of the patient or the animal to be corrected. For example, the subject may include the spine, an upper limb bone, an olecranon fracture, an ulna, phalanges of fingers, metatarsal bones, thigh bone, an ossa cruris, an ankle joint, or the like, or any combination thereof.

In some embodiments, the 3D model associated with the subject may include a 3D model of the whole or a portion of the patient or the animal. For example, the 3D model associated with the subject may be a 3D model of a human body or an animal body, a 3D model of a leg, a 3D model of a spine, or the like. A size of the 3D model associated with the subject may be relating to an actual size of the subject. For example, the size of the 3D model may be determined by scaling (e.g., scaling down or scaling up) the actual size of the subject proportionally.

In some embodiments, the processing device 114 may obtain the 3D model associated with the subject uploaded by a 3D camera device (e.g., a 3D scanner). The 3D model may be obtained by scanning the subject via the 3D camera device (e.g., the 3D scanner). In some embodiments, the processing device 114 may obtain the 3D model associated with the subject from a terminal device (e.g., the terminal device 130) via the network 120. For example, a user may input a 3D model of the subject to the terminal device (e.g., the terminal device 130) via a network port directly.

In some embodiments, the processing device 114 may obtain image data (e.g., a plurality of medical images) associated with the subject. For example, the processing device 114 may obtain the image data from the data obtaining device 110 directly via the network 120. As another example, the processing device 114 may obtain the image data from a database based on identification information of the subject input by a user. The identification information of the subject may include an identification (ID) number of the subject, a name of the subject, the gender of the subject, the age of the subject, a portion of the subject to be corrected, or the like, or any combination thereof. In some embodiments, the database may include a medical imaging information system. For example, the database may be a picture archiving and communication system (PACS). The PACS may refer to a medical imaging technology which provides economical storage and convenient access to images from multiple modalities (source machine types). In some embodiments, the PACS may store a plurality of images (e.g., a plurality of medical images) generated by a plurality of medical devices (e.g., a nuclear magnetic resonance (NMR), a computer tomography (CT) device, a digital X-ray (DR) device, an ultrasound device, an X-ray imaging device) in a medical imaging department of a hospital. The format for PACS image storage and transfer may be digital imaging and communications in medicine (DICOM).

The processing device 114 may determine the 3D model associated with the subject by processing the image data associated with the subject. For example, the processing device 114 may determine a target area by performing an image segmentation operation on the image data associated with the subject. The processing device 114 may extract body surface data associated with the target area from the image data associated with the subject. The processing device 114 may generate a plurality of meshes of the 3D model based on the body surface data associated with the target area. More descriptions of obtaining of the 3D model may be found elsewhere in the present disclosure (e.g., FIG. 6 and descriptions thereof).

In some embodiments, an instruction to obtain the 3D model of the subject may be stored in a storage device (e.g., the storage device 150) of the orthosis design system 100, and may be executed by the processing device 114 (e.g., the first obtaining module 401).

In 520, the processing device 114 (e.g., the second obtaining module 402) may obtain one or more reference images associated with the subject.

In some embodiments, the one or more reference images may include a DR image, a CT image, an MR image, or the like, or any combination thereof. For example, the one or more reference images may be two-dimensional DR images (e.g., a DR plain film). In some embodiments, the reference image may include annotation information. The annotation information may include a Cobb angle. As used herein, the Cobb angle may refer to a measurement of the degree of side-to-side spinal curvature. The Cobb angle may describe the maximum distance from straight a scoliotic curve may be. In some embodiments, the degree of spinal curvature of a human (or an animal) may be evaluated based on the Cobb angle. A treatment method (e.g., an orthosis treatment, a surgical treatment) may be determined based on the degree of spinal curvature of the human (or the animal). For example, if the Cobbe angle annotated on the reference image is in a range from 20° to 45°, it may indicate that the degree of spinal curvature is relatively low and an orthosis may be used to correct the spine. If the Cobbe angle exceeds 45°, it may indicate that the degree of spinal curvature is relatively high and a surgical treatment may be performed to correct the spine.

In some embodiments, the processing device 114 may obtain the one or more reference images associated with the subject from the data obtaining device 110 (e.g., a DR device, an X-ray imaging device, a camera). The data obtaining device 110 (e.g., a DR device, an X-ray imaging device, a camera) may perform a laser scanning or an optical scanning on the subject. For example, the data obtaining device 110 (e.g., a DR device, an X-ray imaging device, a camera) may capture a plurality of images associated with the subject, and store the plurality of images in a storage device (e.g., the storage device 150) of the orthosis design system 100. The processing device 114 may access the storage device and retrieve the one or more reference images from the storage device. As another example, the data obtaining device 110 (e.g., a DR device, an X-ray imaging device, a camera) may send one or more captured reference images to the processing device 114 directly.

In some embodiments, the processing device 114 may obtain the one or more reference images based on the identification information of the subject. For example, the processing device 114 may obtain the identification information of the subject (e.g., a patient). The processing device 114 may select one or more images from a plurality of historical images based on the identification information of the subject. The user identification information associated with the selected one or more images may be similar with the identification information of the subject. The processing device 114 may determine the selected one or more images as the one or more reference images of the subject.

In some embodiments, the processing device 114 may obtain the one or more reference images based on a machine learning model. For example, the processing device 114 may determine an image generation model by training a preliminary model based on historical image data. The processing device 114 may obtain the one or more reference images by inputting the identification information of the subject into the image generation model.

In some embodiments, an instruction to obtain the one or more reference images of the subject may be stored in a storage device (e.g., the storage device 150) of the orthosis design system 100, and may be executed by the processing device 114 (e.g., the second obtaining module 402).

In 530, the processing device 114 (e.g., the orthosis design data determination module 403) may determine orthosis design data for the subject based on the 3D model and the one or more reference images.

Figure 8:
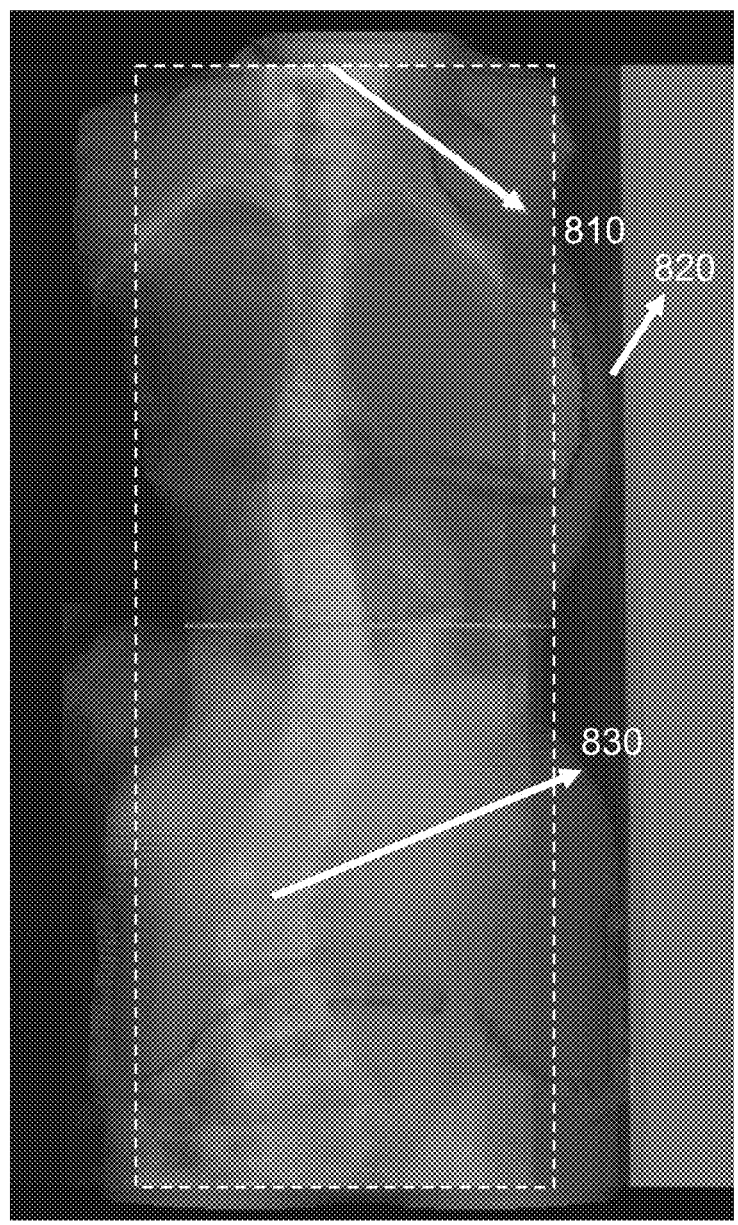
FIG. 8 illustrates an exemplary image of a reference image superimposed on a 3D model according to some embodiments of the present disclosure.

In some embodiments, the orthosis design data may refer to data for designing an orthosis for the subject to be corrected. The orthosis design data may be used to determine the orthosis for the subject. In some embodiments, the orthosis may be an extracorporeal device configured on the subject or a portion thereof to be corrected. In some embodiments, the processing device 114 may compare the 3D model with the reference image(s). For example, the processing device 114 may superimpose the reference image on the 3D model, as illustrated in FIG. 8. Specifically, the processing device 114 may determine one or more first reference points (or one or more first feature points) in the reference image. The processing device 114 may determine one or more second reference points (or one or more second feature points) corresponding to the one or more first reference points in the 3D model. The processing device 114 may superimpose the reference image on the 3D model by aligning the one or more first reference points in the reference image and the one or more corresponding second reference points in the 3D model.

In some embodiments, the processing device 114 may determine the orthosis design data by modifying the 3D model based on a comparison result (e.g., a superimposing result). The orthosis design data for the subject may include a processing result determined by performing a mesh deformation operation, a mesh smoothing operation, a mesh division operation, a mesh splitting operation, or the like, or any combination thereof, on the 3D model.

In some embodiments, the processing device 114 may perform a mesh splitting operation (also referred to as a model splitting operation) on the 3D model to generate a desired shape. For example, the processing device 114 may determine a spline curve associated with the 3D model. For each point of a plurality of points on the spline curve, the processing device 114 may determine a center point corresponding to the point. The processing device 114 may determine a link line connecting the center point and the corresponding point. The processing device 114 may determine a plurality of boundary points along a direction of the link line. The processing device 114 may generate a split surface based on all the boundary points corresponding to the plurality of points on the spline curve. The processing device 114 may split the 3D model based on the split surface. More descriptions for splitting a 3D model may be found elsewhere in the present disclosure (e.g., FIGS. 10-16, and descriptions thereof).

In some embodiments, the orthosis design data may be determined manually by a user (e.g., an orthosis designer). For example, an orthosis designer may modify the 3D model based on the comparison result between the 3D model and the reference image(s) to determine the orthosis design data (e.g., a plurality of parameters associated with the orthosis).

In some embodiments, an instruction to determine the orthosis design data may be stored in a storage device (e.g., the storage device 150) of the orthosis design system 100, and may be executed by the processing device 114 (e.g., the orthosis design data determination module 403).

According to some embodiments of the present disclosure, the reference image(s) and the 3D model of the subject may be obtained by the processing device 114 based on an orthosis design instruction obtained via a network access port. The orthosis (e.g., an orthosis model) may be designed by comparing the reference image(s) of the subject with the 3D model of the subject (e.g., superimposing the reference image(s) on the 3D model). Accordingly, problems of complicated and low efficiency of an orthosis design process in prior arts may be solved. A plurality of users may access the server for designing the orthosis via the network access port to complete the design of the orthosis. The orthosis design process may be simplified, and the efficiency of the orthosis design process may be improved.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, operations 510 and 520 may be combined into one operation. In operation 510, the processing device 114 may obtain the 3D model and the reference image of the subject.

In some embodiments, one or more operations may be added in process 500. For example, an operation for altering the orthosis design data may be added in process 500. More descriptions for altering of the orthosis design data may be found elsewhere in the present disclosure (e.g., FIG. 7 and descriptions thereof).

As another example, an operation for determining housing design data associated with a housing of the orthosis may be added in process 500. In some embodiments, the processing device 114 (e.g., the thickness adjustment module 405) may determine the housing design data associated with the housing of the orthosis by performing a thickness-adjustment operation on the orthosis design data. In some embodiments, the housing design data may represent a size of the orthosis. For example, the housing design data may include a length, a width, a height, a thickness of the orthosis, or the like, or any combination thereof. In some embodiments, the thickness of the orthosis may be in a range from 3 mm to 4 mm. In some embodiments, the processing device 114 (e.g., the storage module 406) may store the housing design data in one or more components (e.g., the terminal device 130, the storage device 150) of the orthosis design system 100. In some embodiments, the processing device 114 (e.g., the uploading module 407) may transmit the housing design data to a server (e.g., a 3D print server).

As still another example, an operation for printing the orthosis may be added in process 500. In some embodiments, the server 144 may be connected to a 3D printing server with a communication protocol directly. The processing device 114 may transmit the orthosis design data, the housing design data, and/or a plurality of 3D printing parameters associated with the orthosis to the 3D printing server. The plurality of 3D printing parameters associated with the orthosis may include a printing material, a printing orientation, a layer thickness, a printing orientation angle, a filling ratio, a filament feed rate, or the like, or any combination thereof. The 3D printing server may be connected to a 3D printing device to print the orthosis based on the housing design data, the orthosis design data, and/or a plurality of 3D printing parameters associated with the orthosis. Accordingly, an orthosis design and print process may be achieved.

According to some embodiments of the present disclosure, the reference image(s) and the 3D model of the subject may be obtained by the processing device 114 based on an orthosis design instruction obtained via a network access port. The orthosis may be designed by comparing the reference image(s) of the subject with the 3D model of the subject (e.g., superimposing the reference image(s) on the 3D model). Data associated with the orthosis (e.g., the orthosis design data, the housing design data) may be transmitted to the 3D printing server, and an orthosis may be printed. Accordingly, the problems of complicated and low efficiency of an orthosis design process in prior arts may be solved. The user may access the server for designing the orthosis and the server for printing the orthosis via the network access port to complete the design and the print of the orthosis. The orthosis design and print process may be simplified, and the efficiency of the orthosis design and print process may be improved.

Figure 6:
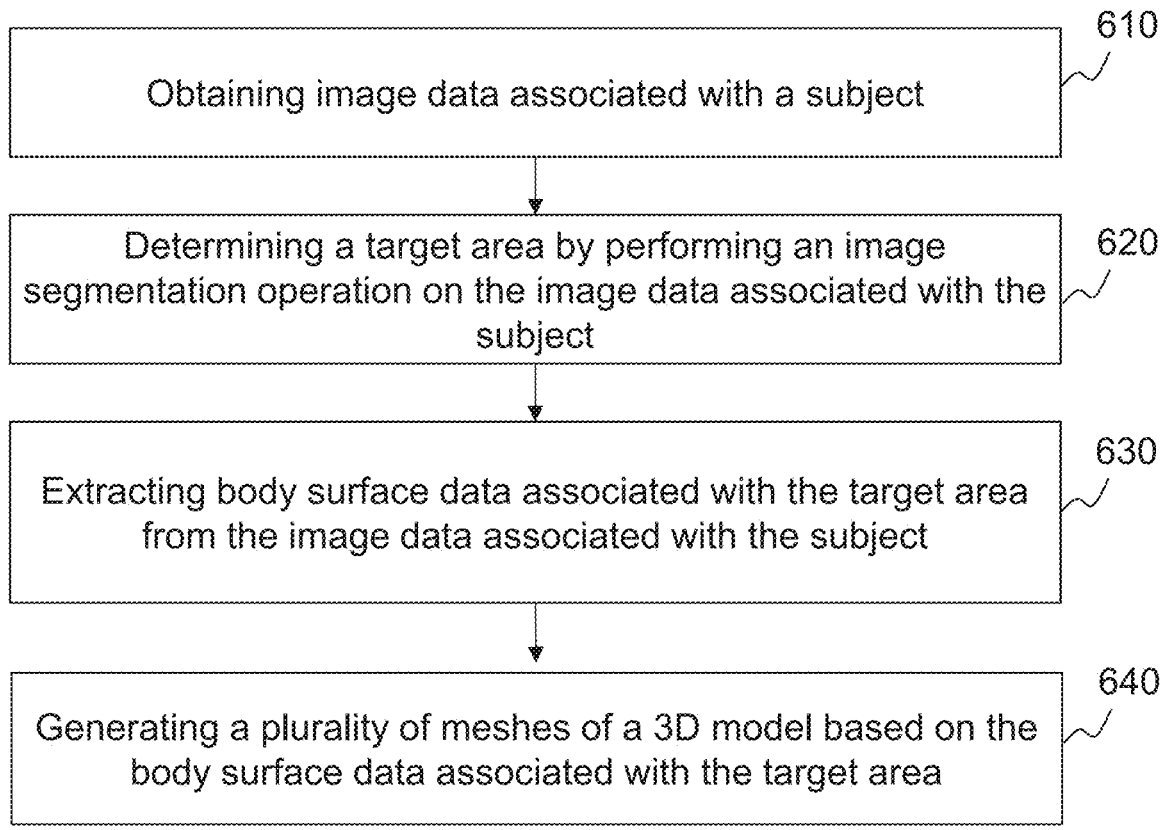
FIG. 6 is a flowchart illustrating an exemplary process for obtaining a 3D model associated with a subject according to some embodiments of the present disclosure.

FIG. 6 is a flowchart illustrating an exemplary process for obtaining a 3D model associated with a subject according to some embodiments of the present disclosure. Process 600 may be executed by the orthosis design system 100. For example, process 600 may be implemented as a set of instructions (e.g., an application) stored in the storage device 150 in the orthosis design system 100. The processing device 114 may execute the set of instructions and accordingly be directed to perform process 600 in the orthosis design system 100. The operations of the illustrated process 600 presented below are intended to be illustrative. In some embodiments, process 600 may be accomplished with one or more additional operations not described, and/or without one or more of the operations discussed. Additionally, the order in which the operations of process 600 as illustrated in FIG. 6 and described below is not intended to be limiting.

In 610, the processing device 114 (e.g., the first obtaining module 401) may obtain image data associated with a subject.

In some embodiments, the image data may include a medical image. For example, the image data may include an MR image, a CT image, a digital X-ray image, a computer X-ray image, or the like, or any combination thereof. In some embodiments, the image data may include a data set of a plurality of tomographic images. The processing device 114 may determine the 3D model based on the data set of the plurality of tomographic images. For example, the processing device 114 may superimpose the plurality of tomographic images to generate the 3D model. In some embodiments, the processing device 114 may obtain the image data from a database (e.g., a PACS), as described elsewhere in the present disclosure (e.g., FIG. 5 and descriptions thereof).

In some embodiments, the image data may be in a form of digital imaging and communications in medicine (DICOM). DICOM may refer to a standard for image data storage and transfer. DICOM may use a specific file format and a communication protocol to define a medical image format that can be used for data exchange with a quality that meets clinical needs. For example, an image (e.g., a medical image) may be saved as a DICOM file format. In some embodiments, a medical imaging device (e.g., a CT device, a DR device, an MRI device, a 3D scanner) may change a format of a medical image to a DICOM file format. A user (e.g., a doctor, an orthosis designer) of the orthosis design system 100 may use a viewer with a function to read a DICOM file, to read the medical image in the DICOM file format, and to determine information associated with the medical image.

In some embodiments, the image data in the DICOM file format may include data related to an image in the DICOM file format, personal information of the subject (e.g., a patient), medical information of the subject, or the like, or any combination thereof. The data related to the image in the DICOM file format may include data associated with a device that captures the image, medical background data (e.g., historical diseases), or the like, or any combination thereof. The personal information of the subject may include a name, the gender, the age, a weight, a height, an identification (ID) number (e.g., an ID card number) of the subject, or the like, or any combination thereof. The medical information may include a medical history of the subject, surgery information, or the like, or any combination thereof. The surgery information may include a start time of a surgery, an estimated end time of the surgery, a surgical operation procedure, or the like, or any combination thereof.

In some embodiments, an instruction to obtain the image data may be stored in a storage device (e.g., the storage device 150) of the orthosis design system 100, and may be execute by the processing device 114 (e.g., the first obtaining module 401).

In some embodiments, the processing device 114 may preprocess the image data. For example, the processing device 114 may perform an image segmentation operation, an image filtering operation, a smoothing operation, a mesh generation operation, or the like, or any combination thereof, on the image data.

In 620, the processing device 114 (e.g., the first obtaining module 401) may determine a target area by performing an image segmentation operation on the image data associated with the subject.

In some embodiments, the image segmentation operation may include a threshold segmentation operation, an edge segmentation operation, a region segmentation operation, a motion segmentation operation, a segmentation operation based on an active contour model, a segmentation operation based on fuzzy clustering algorithm, a segmentation operation based on wavelet transform, or the like, or any combination thereof. In some embodiments, the threshold segmentation operation may include a histogram threshold segmentation operation, an inter-class variance threshold segmentation operation, a two-dimensional maximum entropy image segmentation operation, a fuzzy threshold segmentation operation, or the like, or any combination thereof. In some embodiments, the region segmentation operation may include a region growth operation, a region merging operation, or the like, or any combination thereof. In some embodiments, the target area may include an area to be corrected in the image data. The processing device 114 may perform an image segmentation operation on the image data to obtain the target area.

In some embodiments, an instruction for performing an image segmentation operation on the image data may be stored in a storage device (e.g., the storage device 150) of the orthosis design system 100, and may be executed by the processing device 114 (e.g., the first obtaining module 401).

In 630, the processing device 114 (e.g., the first obtaining module 401) may extract body surface data associated with the target area from the image data associated with the subject.

In some embodiments, the body surface data may include a plurality of pixels of a body surface contour (e.g., a skin contour) obtained from the segmented image data. In some embodiments, the body surface data may include a mask. The mask may include, but is not limited to, a two-dimensional matrix array, a multi-value image, or the like, or any combination thereof. In some embodiments, the processing device 114 may extract the body surface data associated with the target area from the segmented image data.

In some embodiments, the processing device 114 may process the body surface data. For example, the processing device 114 may delete a plurality of noise points (e.g., a plurality of pixels of clothes or accessories) in the body surface data. Accordingly, the processed body surface data may be more suitable for constructing the 3D model. As another example, the processing device 114 may perform a filtering operation, a smoothing operation, a boundary calculation operation, or the like, or any combination thereof, on the body surface data.

In some embodiments, an instruction for extracting body surface data of the target area may be stored in a storage device (e.g., the storage device 150) of the orthosis design system 100, and may be executed by the processing device 114 (e.g., the first obtaining module 401).

In 640, the processing device 114 (e.g., the first obtaining module 401) may generate a plurality of meshes of the 3D model based on the body surface data associated with the target area.

In some embodiments, the mesh may be formed by combining a plurality of feature points of the body surface data associated with the target area. In some embodiments, the feature points may include a plurality of pixels of a body surface contour of the target area. For example, a plurality of feature points of the body surface data may be connected to form a plurality of faces. The plurality of faces may be combined to form the plurality of meshes of the 3D model. In some embodiments, the face may have a shape of a triangle, a quadrilateral, or other concave or convex polygons. Accordingly, the plurality of meshes of the 3D model may be formed by combining the plurality of faces, a rendering process (or a display process) may be simplified.

In some embodiments, an instruction for generating the plurality of meshes may be stored in a storage device (e.g., the storage device 150) of the orthosis design system 100, and may be executed by the processing device 114 (e.g., the first obtaining module 401).

Taking an orthosis design process for a scoliosis patient as an example. The processing device 114 may segment image data associated with a torso of a subject. The processing device 114 may extract body surface data and spine data of the subject. The processing device 114 may process the body surface data. For example, the processing device 114 may perform a smoothing operation, a filtering operation, or a boundary correction operation, on the body surface data, to achieve a good segmentation effect on the body surface data and the spine data. The processing device 114 may generate a plurality of polygon meshes based on the processed body surface data to form a 3D model. In some embodiments, the plurality of polygon meshes may include point cloud data of the subject. The 3D model may be generated based on the point cloud data. As used herein, the point cloud data may refer to the body surface data of the subject.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 410 and 420 may be performed simultaneously.

FIG. 7 is a flowchart illustrating an exemplary process for altering orthosis design data according to some embodiments of the present disclosure. The process 700 may be executed by the orthosis design system 100. For example, process 700 may be implemented as a set of instructions (e.g., an application) stored in the storage device 150 in the orthosis design system 100. The processing device 114 may execute the set of instructions and accordingly be directed to perform the process 700 in the orthosis design system 100. The operations of the illustrated process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 114 (e.g., the altering module 404) may determine, based on the 3D model and the orthosis design data, force data of at least one region of the subject after wearing an orthosis.

In some embodiments, the force data may include a force magnitude and/or a force direction generated by the orthosis on the at least one region of the subject after wearing the orthosis. In some embodiments, the processing device 114 may determine the force data by performing one or more simulation experiments. For example, the processing device 114 may generate a 3D orthosis model based on the orthosis design data. The processing device 114 may simulate force data generated by the 3D orthosis model on the 3D model of the subject after wearing the 3D orthosis model. For example, the processing device 114 may simulate a curvature degree of at least one mesh of the 3D model of the subject after wearing the orthosis. The processing device 114 may determine the force data based on the bending degree of the at least one mesh of the 3D model of the subject.

In some embodiments, the force data (e.g., the force magnitude, the force direction) generated by the 3D orthosis model on different regions of the 3D model of the subject may be different. For example, the processing device 114 may determine the force data of a plurality of meshes of the 3D model of the subject by simulating the force data of the at least one region of the subject after wearing the orthosis. In some embodiments, the processing device 114 may display different force data (e.g., different magnitudes of force) in different colors. For example, the processing device 114 may determine preset force data for the plurality of meshes of the 3D model of the subject. The processing device 114 may display different preset force data in different colors. The preset force data for a mesh of the 3D model of the subject may refer to a force generated by the 3D orthosis model on the mesh. For illustration purposes, if the force applied on a mesh is relatively large, the processing device 114 may display the mesh in a red color. If the force applied on a mesh is relatively low, the processing device 114 may display the mesh in a blue color.

In some embodiments, an instruction for simulating the force data may be stored in a storage device (e.g., the storage device 150) of the orthosis design system 100, and may be executed by the processing device 114 (e.g., the altering module 404).

In 720, the processing device 114 (e.g., the altering module 404) may alter, based on the force data of the at least one region of the subject, the orthosis design data.

In some embodiments, the processing device 114 may alter the orthosis design data based on the force data of the at least one region of the subject. For example, the processing device 114 may alter the orthosis design data based on the force magnitudes and force directions of the plurality of meshes of the 3D model of the subject, and an applied force of the 3D orthosis model. In some embodiments, the applied force of the 3D orthosis model may refer to a force of a pressure region of the orthosis applied on different regions of the subject during the correcting of the subject. In some embodiments, the applied force may be determined according to statistical clinical data. In some embodiments, the applied force may be determined based on a trained machine learning model.

For illustration purposes, a process for altering the orthosis design data may be taken as an example. When a 3D model of the subject does not wear the 3D orthosis model, a triangular face on the 3D model of the subject is at a position of d and the force is 0. After the 3D model of the subject wears the 3D orthosis model, the triangular face is at a position of e, and the force is A. The preset applied force of the 3D orthosis model on the triangular face is B. The value of B is different from the value of A. If B is greater than A, it may indicate that the force applied on the triangular face is relatively low after the 3D orthosis model is worn on the 3D model of the subject. The processing device 114 may mark the position of e in a blue color. The orthosis design data may need to be altered to increase the force applied on the triangular face. That is, a curvature degree of one or more meshes in the triangle face may need to be increased. During the altering of the orthosis design data, the color of the position of e may change from blue to light blue or transparent gradually, as the force applied on the triangular face increases. If B is less than A, it may indicate that the force applied on the triangle face is relatively large after the 3D orthosis model is worn on the 3D model of the subject. The processing device 114 may mark the position of e in a red color. The orthosis design data may need to be altered to reduce the force applied on the triangle face. That is, a curvature degree of one or more meshes in the triangle face may need to be reduced. During the altering of the orthosis design data, the color of the position of e may change from red to light red or transparent gradually, as the force applied on the triangular face decreases. By adjusting the orthosis design data, the force A generated by the 3D orthosis model on the triangular face may be equal to (or substantially equal to) the preset applied force B, so that the force of the triangular face at the position of e may be equal to (or substantially equal to) the applied force. Similarly, the processing device 114 may alter the orthosis design data by correcting the plurality of meshes (or a plurality of pressure regions) of the 3D model of the subject. Accordingly, the orthosis determined based on the altered orthosis design data may match the subject closely, and a correction effect of the orthosis may be ensured.

In some embodiments, after the orthosis design data is altered by the processing device 114, the altered orthosis design data may further be confirmed by the user of the orthosis design system 100. For example, if the altered orthosis design data cannot meet a correction requirement, the user may further modify the alter orthosis design data. In some embodiments, a user (e.g., a doctor, an orthosis designer) of the orthosis design system 100 may alter the orthosis design data based on the force data of the at least one region of the subject after wearing the orthosis.

In some embodiments, an instruction to obtain the altered orthosis design data may be stored in a storage device (e.g., the storage device 150) of the orthosis design system 100, and may be executed by the processing device 114 (e.g., the altering module 404).

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, in 710, the processing device 114 may determine the force data of the at least one region of the subject after wearing the orthosis based on a trained machine learning model. For example, the processing device 114 may input the orthosis design data and the 3D model of the subject into the trained machine learning model. The trained machine learning model may output the force data of the at least one region of the subject after wearing the orthosis.

FIG. 8 illustrates an exemplary image of a reference image superimposed on a 3D model according to some embodiments of the present disclosure.

As shown in FIG. 8, 810 refers to a reference image (e.g., a DR image) of a subject, and 820 refers to a 3D model of the subject. The reference image 810 may reflect a degree of scoliosis of the subject, as shown in a position 830 in the reference image 810. The processing device 114 may superimpose the reference image 810 on the 3D model 820. The processing device 114 may determine orthosis design data by modifying the 3D model 820 based on a superimposing result, as described elsewhere in the present disclosure (e.g., FIG. 5 and descriptions thereof).

Figure 9:
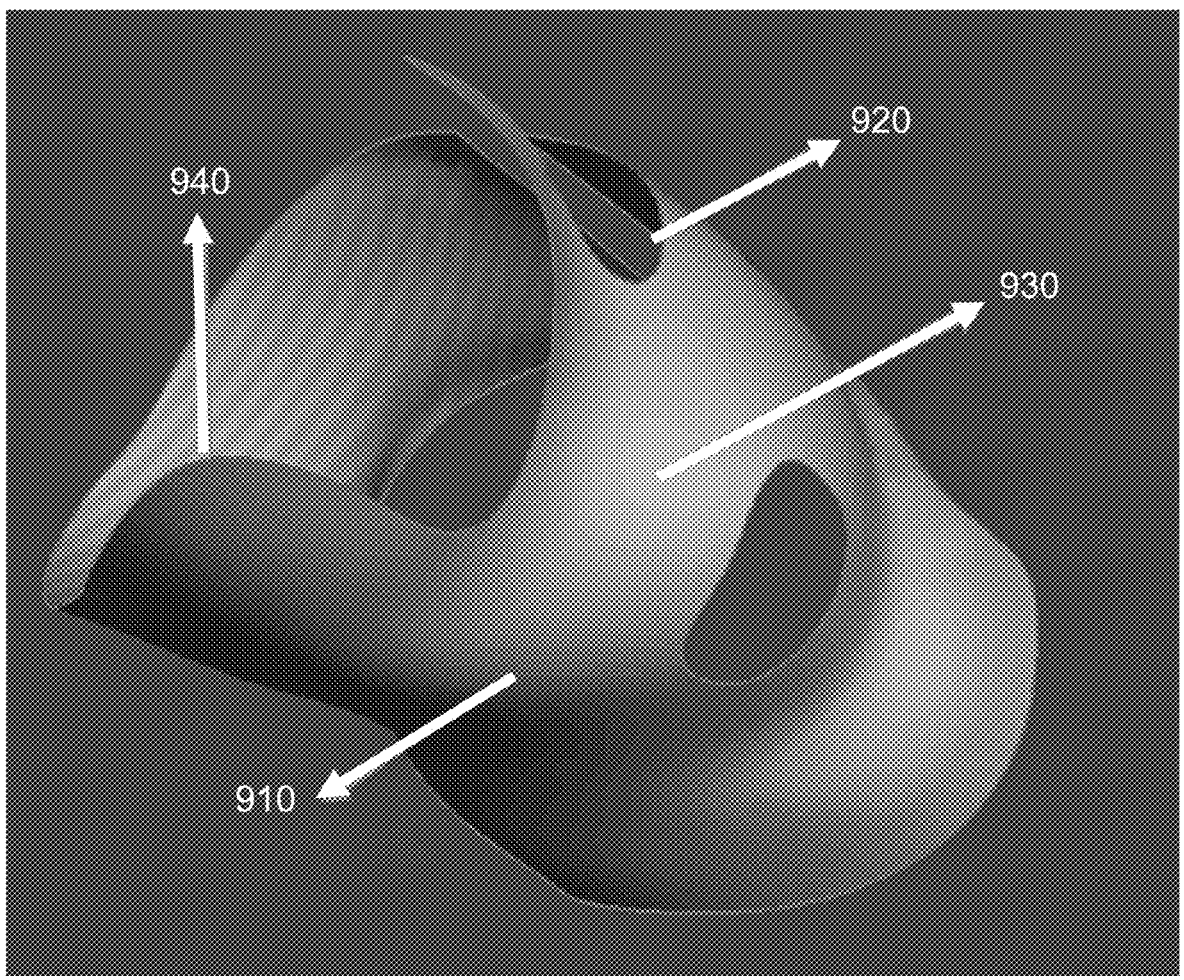
FIG. 9 is a schematic diagram illustrating a housing of an orthosis according to some embodiments of the present disclosure.

FIG. 9 is a schematic diagram illustrating a housing of an orthosis according to some embodiments of the present disclosure.

In some embodiments, the processing device 114 may perform one or more processing operations on orthosis design data based on correction needs of different regions of a subject. For example, as shown in FIG. 9, the processing device 114 may perform a mesh deformation operation on a pressure region 910 of the orthosis. As another example, the processing device 114 may perform a mesh splitting operation on an edge and/or an opening of the orthosis, as shown in a region 920 in FIG. 9. As still another example, the processing device 114 may perform a mesh smoothing and/or a mesh division operation on one or more other regions 930 of the orthosis. In some embodiments, the processing device 114 may determine housing design data associated with a housing of the orthosis by performing a thickness-adjustment operation on the orthosis design data, as described elsewhere in the present disclosure. The housing design data may be used to determine the housing of the orthosis with a certain thickness, as shown in a position 940 in FIG. 9.

Figure 10:
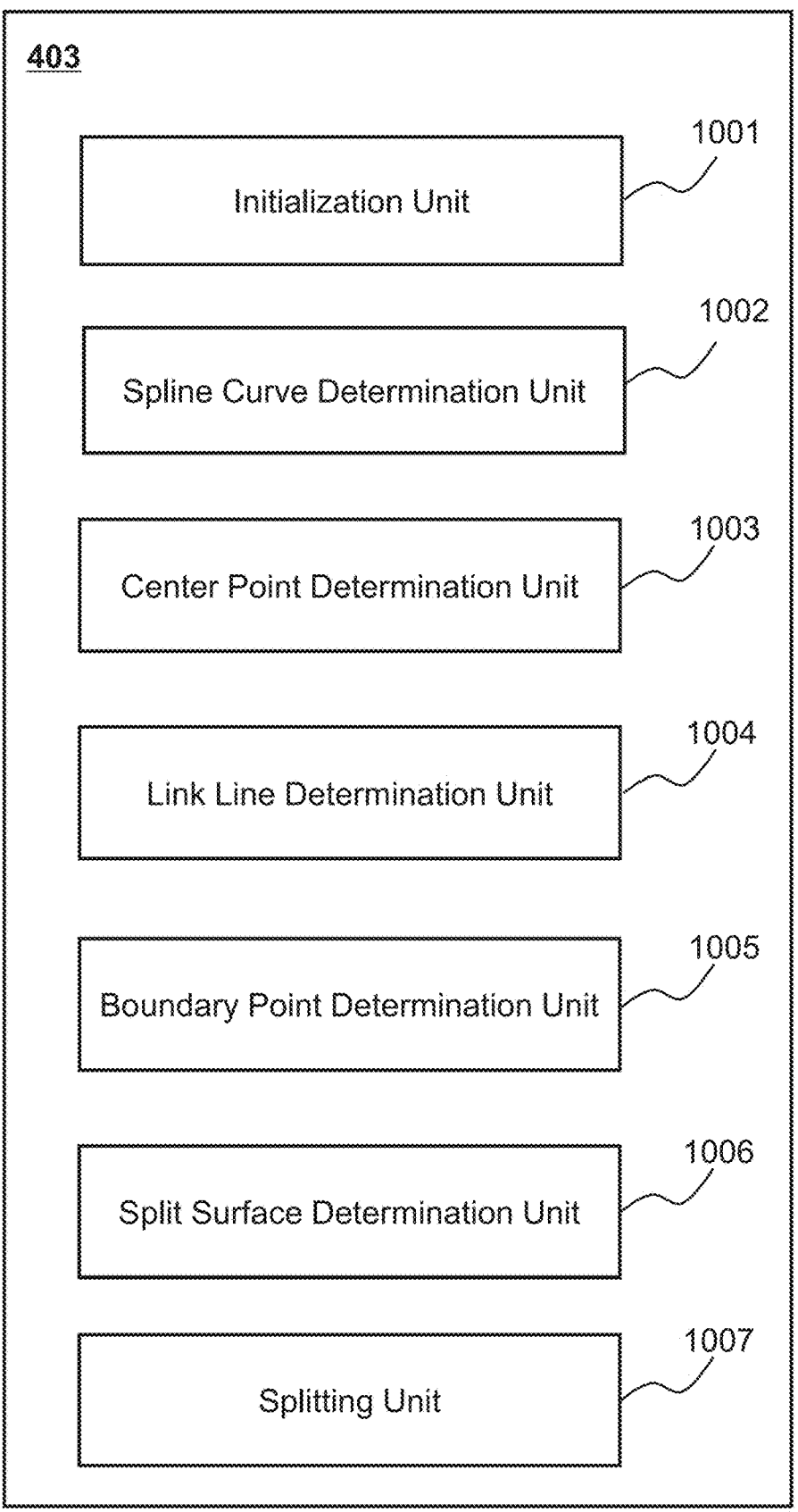
FIG. 10 is a block diagram illustrating an exemplary orthosis design data determination module according to some embodiments of the present disclosure.

FIG. 10 is a block diagram illustrating an exemplary orthosis design data determination module according to some embodiments of the present disclosure. The orthosis design data determination module 403 may include an initialization unit 1001, a spline curve determination unit 1002, a center point determination unit 1003, a link line determination unit 1004, a boundary point determination unit 1005, a split surface determination unit 1006, and a splitting unit 1007. The units may be hardware circuits of at least part of the orthosis design data determination module 403. The units may also be implemented as an application or set of instructions read and executed by the orthosis design data determination module 403. Further, the units may be any combination of the hardware circuits and the application/instructions. For example, the units may be part of the orthosis design data determination module 403 when the orthosis design data determination module 403 is executing the application or set of instructions.

The initialization unit 1001 may be configured to initialize a 3D model. In some embodiments, the initialization unit 1001 may obtain data associated with a 3D model. In some embodiments, the initialization unit 1001 may initialize camera parameters. In some embodiments, the initialization unit 1001 may determine an initial transformation matrix between a model coordinate system and a world coordinate system. In some embodiments, the initialization unit 1001 may render a 3D model based on data associated with the 3D model. More descriptions of the initialization of the 3D model may be found elsewhere in the present disclosure (e.g., FIG. 11, and descriptions thereof).

The spline curve determination unit 1002 may be configured to determine a spline curve associated with a 3D model. In some embodiments, the spline curve determination unit 1002 may obtain a plurality of first coordinates input by a user. In some embodiments, the spline curve determination unit 1002 may determine a plurality of third coordinates by performing a spline interpolation operation on a plurality of first coordinates. In some embodiments, the spline curve determination unit 1002 may determine a plurality of second coordinates by projecting a plurality of third coordinates on the 3D model. For example, the spline curve determination unit 1002 may transform a plurality of third coordinates in a screen coordinate system to a plurality of fourth coordinates in a view coordinate system. The spline curve determination unit 1002 may transform the plurality of fourth coordinates in the view coordinate system to a plurality of fifth coordinates in a camera coordinate system. The spline curve determination unit 1002 may transform the plurality of fifth coordinates in the camera coordinate system to a plurality of sixth coordinates in the world coordinate system. The spline curve determination unit 1002 may transform the plurality of sixth coordinates in the world coordinate system to the plurality of second coordinates in the model coordinate system. In some embodiments, the spline curve determination unit 1002 may determine a spline curve by connecting a plurality of second coordinates. More descriptions of the determination of the spline curve may be found elsewhere in the present disclosure (e.g., FIGS. 11, 12, 13, and descriptions thereof).

The center point determination unit 1003 may be configured to determine a center point corresponding to a point (e.g., a second coordinate) on a spline curve associated with a 3D model. In some embodiments, the center point determination unit 1003 may determine a center point corresponding to a point on a spline curve based on model coordinates of the point. In some embodiments, the center point determination unit 1003 may determine a center point corresponding to a point on a spline curve by projecting the point on a Z-axis of a model coordinate system. More descriptions of the determination of the center point may be found elsewhere in the present disclosure (e.g., FIGS. 11, 14, and descriptions thereof).

The link line determination unit 1004 may be configured to determine a link line connecting a center point and a corresponding point (e.g., a second coordinate) on a spline curve associated with a 3D model. In some embodiments, the link line determination unit 1004 may draw a straight line passing through a center point and a corresponding point on a spline curve. More descriptions of the determination of the link line may be found elsewhere in the present disclosure (e.g., FIGS. 11, 14, and descriptions thereof).

The boundary point determination unit 1005 may be configured to determine a plurality of boundary points along a direction of a link line for a point (e.g., a second coordinate) on a spline curve associated with a 3D model. In some embodiments, the plurality of boundary points may include an inner boundary point and an outer boundary point. The inner boundary point may be located inside a 3D model. The outer boundary point may be located outside the 3D model. In some embodiments, the boundary point determination unit 1005 may determine an inner boundary point by extending a second coordinate to the inside of a 3D model along a direction of a link line. In some embodiments, the boundary point determination unit 1005 may determine an outer boundary point by extending a second coordinate to the outside of the 3D model along a direction of a link line. More descriptions of the determination of the plurality of boundary points may be found elsewhere in the present disclosure (e.g., FIG. 11, and descriptions thereof).

The split surface determination unit 1006 may be configured to generate a split surface. In some embodiments, the split surface determination unit 1006 may generate a split surface based on all boundary points corresponding to a plurality of points (e.g., a plurality of second coordinates) on a spline curve. For example, the split surface determination unit 1006 may generate a plurality of split sub-surfaces by alternately connecting a plurality of inner boundary points and a plurality of outer boundary points corresponding to a plurality of second coordinates. As another example, the split surface determination unit 1006 may generate a split surface by combining a plurality of split sub-surfaces. More descriptions of the generation of the split surface may be found elsewhere in the present disclosure (e.g., FIGS. 11, 15A, 15B, and descriptions thereof).

The splitting unit 1007 may be configured to split a 3D model based on a split surface. In some embodiments, the splitting unit 1007 may generate at least two sub-models by splitting a 3D model based on a split surface. In some embodiments, the splitting unit 1007 may render at least one sub-model (e.g., a desired model). In some embodiments, the splitting unit 1007 may display at least one rendered sub-model (e.g., a desired model) on a terminal device (e.g., the terminal device 130) associated with a user. More descriptions for splitting the 3D model may be found elsewhere in the present disclosure (e.g., FIGS. 11, 16, and descriptions thereof).

It should be noted that the above description of the orthosis design data determination module 403 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more units may be combined into a single unit. For example, the center point determination unit 1003, the link line determination unit 1004, the boundary point determination unit 1005, and the split surface determination unit 1006 may be combined into a single unit. In some embodiments, one or more units may be added or omitted in the orthosis design data determination module 403. For example, the orthosis design data determination module 403 may further include a storage unit (not shown in FIG. 10) configured to store data and/or information (e.g., a spline curve, a center point, a link line) associated with the orthosis design system 100. As another example, the initialization unit 1001 may be omitted.

Figure 11:
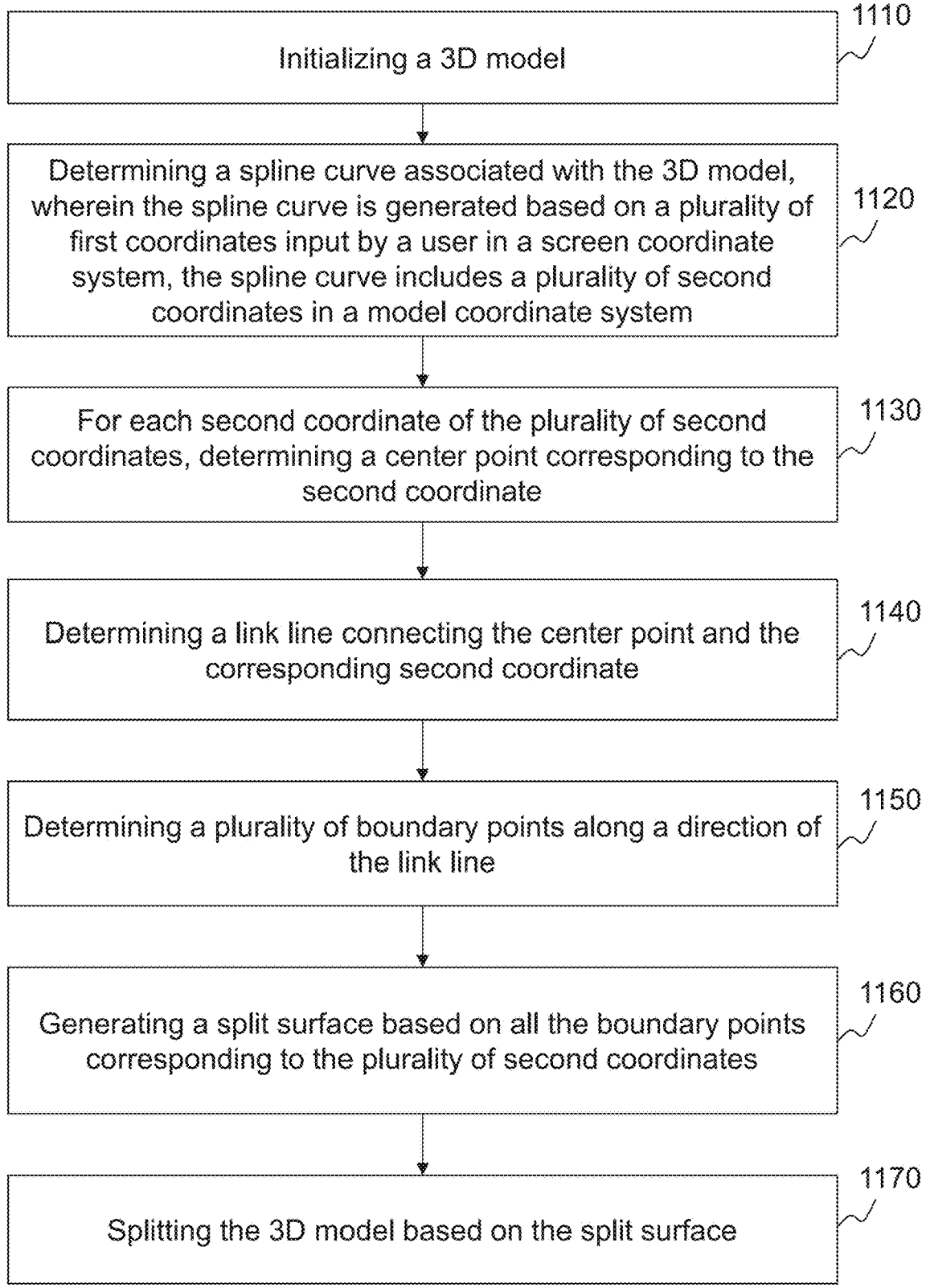
FIG. 11 is a flowchart illustrating an exemplary process for splitting a 3D model according to some embodiments of the present disclosure.

FIG. 11 is a flowchart illustrating an exemplary process for splitting a 3D model according to some embodiments of the present disclosure. Process 1100 may be executed by the orthosis design system 100. For example, process 1100 may be implemented as a set of instructions (e.g., an application) stored in the storage device 150 in the orthosis design system 100. The processing device 114 may execute the set of instructions and may accordingly be directed to perform process 1100 in the orthosis design system 100. The operations of the illustrated process 1100 presented below are intended to be illustrative. In some embodiments, process 1100 may be accomplished with one or more additional operations not described, and/or without one or more of the operations discussed. Additionally, the order in which the operations of process 1100 as illustrated in FIG. 11 and described below is not intended to be limiting.

In 1110, the processing device 114 (e.g., the initialization unit 1001) may initialize a 3D model.

In some embodiments, the 3D model may include a 3D model of a subject, a 3D model of an orthosis, or the like, as described elsewhere in the present disclosure. In some embodiments, the processing device 114 may obtain data associated with the 3D model. The data associated with the 3D model may be used to construct the 3D model. In some embodiments, the 3D model may be a 3D mesh structure where a plurality of 3D points (or vertices) are connected via edges (or lines) and faces (or polygons). In some embodiments, the data associated with the 3D model may include point data, line data, face data, or the like, or any combination thereof. The point data may include position information of a point, e.g., a position, an orientation, a distance between a point and another point. The line data may represent data of a plurality of lines, each of which connects various points. The line data may include point data that a line includes, position information of a line (e.g., a position represented by positions of two vertices, an orientation of a line, a distance between a line and another line), length information of a line, etc. The face data may represent data of one or more faces, each of which formed by lines and/or points. The face data may include point data, line data that a face includes, position information of a face (e.g., a position of a face, an orientation of a face, a distance between a face and another face), a size of a face, a shape of a face (e.g., a triangle shape, a quadrilateral shape, a hexagon shape), etc.

In some embodiments, a position of a point in the 3D model may be represented by model coordinates in a model coordinate system. The model coordinate system may refer to a coordinate system that describes shapes of a subject (e.g., a 3D model). In some embodiments, different model coordinate systems may be constructed for different 3D models. For example, for the model coordinate system of the 3D model in some embodiments of the present disclosure, an origin may be a center point of the 3D model. The X-axis may be from a left side to a right side of the 3D model viewed from a direction facing the front of the 3D model. The Y-axis may be from a front side to a rear side of the 3D model. The Z axis direction may be from a lower side to an upper side of the 3D model.

In some embodiments, the processing device 114 may obtain the data associated with the 3D model from a storage device (e.g., the storage device 150) of the orthosis design system 100, or an external storage device. For example, the processing device 114 may obtain the data associated with the 3D model from a surface mesh stored in the storage device 150. As used herein, the surface mesh may refer to a representation of a surface that includes vertices, edges and faces. In some embodiments, the surface mesh may store the data associated with the 3D model in a 3D file format. Exemplary 3D file formats may include STL, OBJ, FBX, COLLADA, 3DS, IGES, STEP, VRML/X3D, etc.

In some embodiments, the processing device 114 may initialize one or more camera parameters. Exemplary camera parameters may include intrinsic parameters, extrinsic parameters, distortion parameters, etc. The intrinsic parameters of a camera may represent the optical, geometric, and digital characteristics of the camera. For example, the intrinsic parameters of a camera may include a camera focal length, an optical center, etc. The extrinsic parameters of a camera may represent the relative location and orientation of the camera with respect to a world coordinate system. As used herein, the world coordinate system may refer to a fixed coordinate system for representing a subject in the world. For example, the extrinsic parameters of a camera may include a tilt angle of the camera, a yaw angle of the camera, a height of the camera above a plane of the scene captured by the camera, etc. The distortions of a camera may be caused by characteristics of optical lens of the camera and assembly errors; and the distortion parameters quantitatively reflect the distortion. For example, the distortion parameters of a camera may include a radial distortion coefficient, a tangential distortion coefficient, etc.

In some embodiments, the initialized camera parameters may be used to perform a transformation between camera coordinates denoted by a camera coordinate system and world coordinates denoted by the world coordinate system. As used herein, the camera coordinate system may refer to a coordinate system that uses the camera center as its origin and the optic axis as the Z-axis. The X-axis and Y-axis of the camera coordinate system may define an image plane. In some embodiments, the initialized camera parameters may be default parameter stored in a storage device (e.g., the storage device 150). In some embodiments, the initialized camera parameters may be set manually by a user (e.g., an orthosis designer, a doctor) of the orthosis design system 100, or determined by one or more components (e.g., the processing device 114) of the orthosis design system 100 according to different situations. For example, the initialized distortion parameters of the camera may be set as 0.

In some embodiments, the processing device 114 may determine an initial transformation matrix between the model coordinate system and the world coordinate system. The initial transformation matrix may be used to perform a transformation between world coordinates denoted by the world coordinate system and model coordinates denoted by the model coordinate system.

In some embodiments, the processing device 114 may display the 3D model on a screen of the terminal device 130. For example, the processing device 114 may display a front view of the 3D model on the screen of the terminal device 130. In some embodiments, a plurality of points of the 3D model represented by a plurality of model coordinates may be transformed to a plurality of screen coordinates denoted by a screen coordinate system for display. As used herein, the screen coordinate system may refer to physical coordinates of pixels on a computer screen, based on a screen resolution. For the screen coordinate system, an origin may be an upper-left corner point of the screen. The X-axis may be from a left side to a right side of the screen, the Y-axis may be from an upper side to a lower side of the screen. In some embodiments, the processing device 114 may transform the plurality of model coordinates to the plurality of screen coordinates based on the initialized camera parameters and the initial transformation matrix. For example, the plurality of model coordinates may be transformed to a plurality of world coordinates based on the initial transformation matrix. The plurality of world coordinates may be transformed to a plurality of camera coordinates based on the initialized camera parameters. The plurality of camera coordinates may be transformed to a plurality of view coordinates. The plurality of view coordinates may be transformed to the plurality of screen coordinates. More descriptions of the coordinate transformations may be found elsewhere in the present disclosure (e.g., FIG. 13 and descriptions thereof).

In some embodiments, the processing device 114 may render the 3D model based on the data associated with the 3D model. As used herein, rendering may refer to a process of generating a photorealistic or non-photorealistic image from a 2D or 3D model. In some embodiments, the processing device 114 may transform the data associated with the 3D model stored in the surface mesh to a format that can be rendered. For example, the processing device 114 may transform the data associated with the 3D model stored in the surface mesh from the STL format to a polydata format. As used herein, polydata may refer to a surface mesh structure that can hold data arrays in points, cells or in the dataset itself. The processing device 114 may render the 3D model based on the data associated with the 3D model with the polydata format according to one or more rendering algorithms. Exemplary rendering algorithms may include a scanline rendering algorithm, a ray tracing algorithm, a luminous energy radiosity algorithm, a physically based rendering technique, a light field rendering technique, or the like, or any combination thereof.

In 1120, the processing device 114 (e.g., the spline curve determination unit 1002) may determine a spline curve associated with the 3D model.

In some embodiments, a spline curve may refer to a mathematical representation for which it is easy to build an interface that will allow a user to design and control the shape of complex curves and surfaces. In some embodiments, the processing device 114 may determine the spline curve based on a plurality of first coordinates input by a user in a screen coordinate system. In the present disclosure, each first coordinate may correspond to a point input by the user, and the plurality of first coordinates may correspond to a plurality of points input by the user. For example, in the screen coordinate system, a position of a point may be represented by an X-axis coordinate and a Y-axis coordinate. The X-axis coordinate and the Y-axis coordinate of the point may be referred to as a coordinate of the point.

For example, the processing device 114 may obtain a plurality of first points input by the user via a terminal device (e.g., the terminal device 130). Each first point may be represented by screen coordinates in the screen coordinate system. The processing device 114 may perform a spline interpolation operation on the plurality of first points to determine a plurality of interpolation points. Each interpolation point may be represented by screen coordinates in the screen coordinate system. The processing device 114 may project the plurality of interpolation points on the 3D model to determine a plurality of second points. Each second point may be represented by model coordinates in a model coordinate system. The processing device 114 may connect the plurality of second points to generate the spline curve on the 3D model. More descriptions of the determination of the spline curve may be found elsewhere in the present disclosure (e.g., FIG. 12, and descriptions thereof).

In some embodiments, the processing device 114 may obtain the plurality of first points inputted by the user. The processing device 114 may project the plurality of first points on the 3D model to determine a plurality of projection points. Each projection point may be represented by model coordinates in the model coordinate system. The processing device 114 may perform a spline interpolation operation on the plurality of projection points to determine the plurality of second points. The processing device 114 may connect the plurality of second points to generate the spline curve on the 3D model.

In 1130, for each second coordinate of the plurality of second coordinates, the processing device 114 (e.g., the center point determination unit 1003) may determine a center point corresponding to the second coordinate.

In the present disclosure, each second coordinate may correspond to a point on the spline curve, and the plurality of second coordinates may correspond to a plurality of points on the spline curve of the 3D model. For example, in the model coordinate system, a position of a point may be represented by an X-axis coordinate, a Y-axis coordinate, and a Z-axis coordinate. The X-axis coordinate, the Y-axis coordinate, and the Z-axis coordinate of the point may be referred to as a coordinate of the point.

In some embodiments, the processing device 114 may determine a center point corresponding to a point on the spline curve based on model coordinates of the point. For example, the processing device 114 may determine the center point corresponding to the point by determining a value of X-axis coordinate and a value of Y-axis coordinate of the point as 0. For illustration purposes, if model coordinates of a specific point is (X1, Y1, Z1), the processing device 114 may set X1 and Y1 as 0, to determine model coordinates of a center point corresponding to the specific point. That is, the model coordinates of the center point may be (0, 0, Z1).

Figure 14:
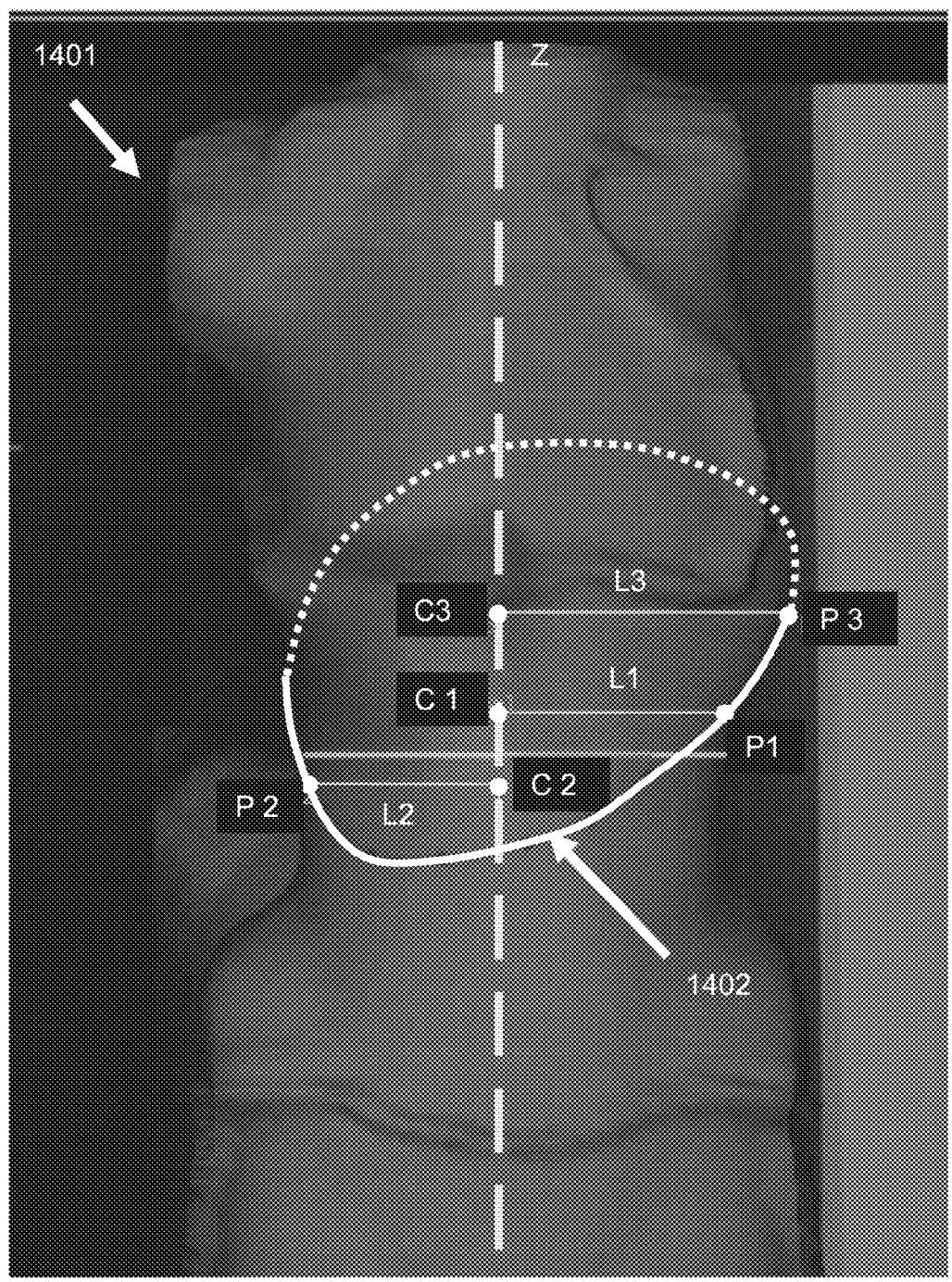
FIG. 14 is a schematic diagram illustrating an exemplary process for determining a center point according to some embodiments of the present disclosure.

In some embodiments, the processing device 114 may determine the center point corresponding to the point by projecting the point on a Z-axis of the model coordinate system. For example, the processing device 114 may project the point (e.g., a point 1, a point 2, a point 3, as illustrated in FIG. 14) on the Z axis of the model coordinate system, to generate a projection point (e.g., a center 1, a center 2, a center 3, as illustrated in FIG. 14). The processing device 114 may determine the projection point as the center point corresponding to the point.

In 1140, for each second coordinate of the plurality of second coordinates, the processing device 114 (e.g., the link line determination unit 1004) may determine a link line connecting the center point and the corresponding second coordinate.

In some embodiments, the link line (e.g., a link line L1, a link line L2, a link line L3 as illustrated in FIG. 14) may refer to a straight line passing through the second coordinate and the corresponding center point. In some embodiments, the processing device 114 may automatically connect the second coordinate and the corresponding center point to generate the link line. In some embodiments, a user (e.g., an orthosis designer) of the orthosis design system 100 may manually connect the second coordinate and the corresponding center point to generate the link line.

In 1150, for each second coordinate of the plurality of second coordinates, the processing device 114 (e.g., the boundary point determination unit 1005) may determine a plurality of boundary points along a direction of the link line.

Figure 15A:
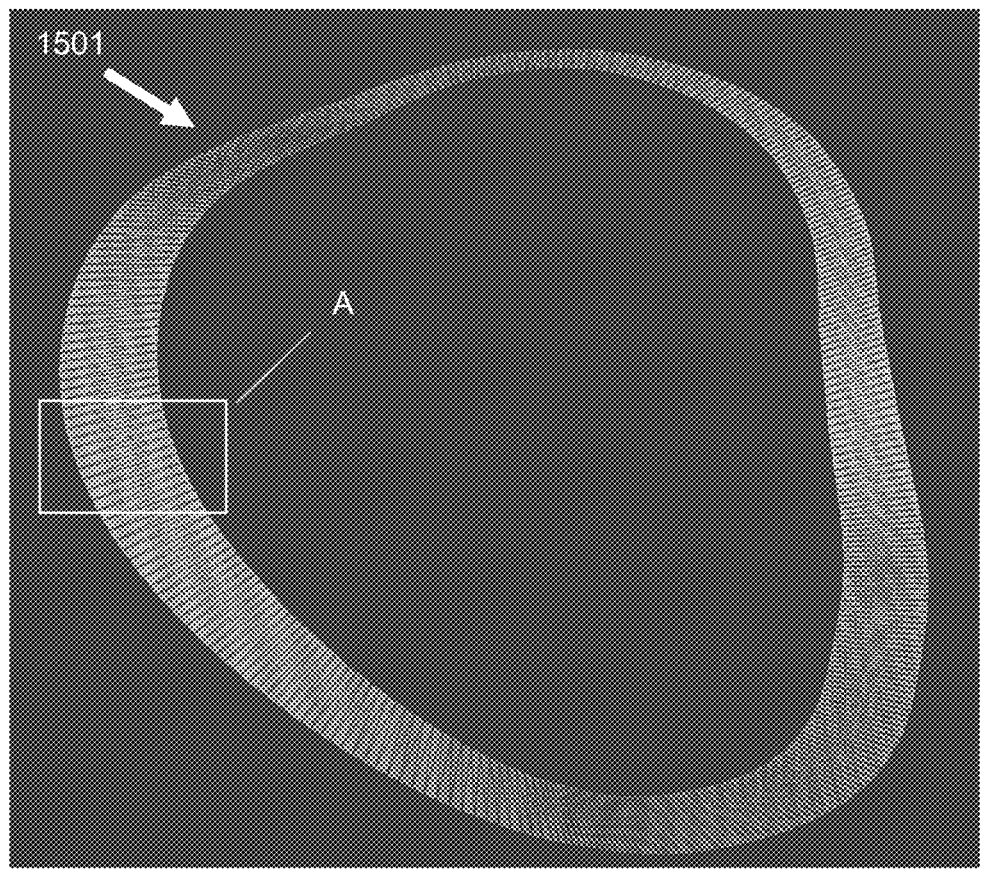
FIG. 15A is a schematic diagram illustrating an exemplary split surface according to some embodiments of the present disclosure.
Figure 15B:
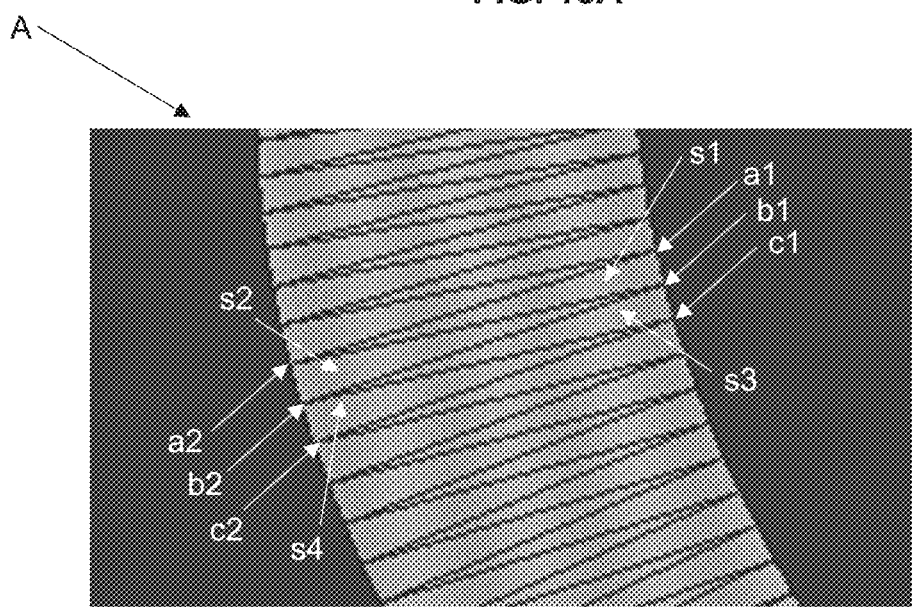
FIG. 15B is an enlarged view of a region A shown in FIG. 15A according to some embodiments of the present disclosure.

In some embodiments, the plurality of boundary points may include an inner boundary point (e.g., a point a1, a point b1, a point c1, as illustrated in FIG. 15B) and an outer boundary point (e.g., a point a2, a point b2, a point c2, as illustrated in FIG. 15B). The inner boundary point may be located inside the 3D model. The outer boundary point may be located outside the 3D model.

The processing device 114 may determine the inner boundary point by extending the second coordinate to the inside of the 3D model along the direction of the link line. For example, the processing device 114 may extend the second coordinate to the inside of the 3D model in a first extension distance along the direction of the link line. The processing device 114 may determine the outer boundary point by extending the second coordinate to the outside of the 3D model along the direction of the link line. For example, the processing device 114 may extend the second coordinate to the outside of the 3D model in a second extension distance along the direction of the link line.

The first extension distance may be the same as or different from the second extension distance. The first extension distance (and/or the second extension distance) may be default parameter stored in a storage device (e.g., the storage device 150). In some embodiments, the first extension distance (and/or the second extension distance) may be set manually by a user (e.g., an orthosis designer, a doctor) of the orthosis design system 100, or determined by one or more components (e.g., the processing device 114) of the orthosis design system 100 according to different situations. For example, the first extension distance (and/or the second extension distance) may be determined based on a size (e.g., a length, a width) of the 3D model. In some embodiments, a relatively large size of the 3D model may correspond to a relatively large first extension distance and/or a relatively large second extension distance.

In 1160, the processing device 114 (e.g., the split surface determination unit 1006) may generate a split surface based on all the boundary points corresponding to the plurality of second coordinates.

In some embodiments, the processing device 114 may generate a plurality of split sub-surfaces by connecting the inner boundary points and the outer boundary points corresponding to the plurality of second coordinates. The split sub-surface may have any shape. For example, the split sub-surface may have a polygonal shape, such as a regular triangle, a rectangle, a square, or a regular hexagon. The processing device 114 may generate the split surface by combining the plurality of split sub-surfaces.

For illustration purposes, assuming that a spline curve includes a plurality of points, e.g., a point a, a point b, . . . , and a point n, the processing device 114 may determine an inner boundary point a1 and an outer boundary point a2 for the point a, an inner boundary point b1 and an outer boundary point b2 for the point b, . . . , an inner boundary point n1 and an outer boundary point n2 for the point n. The processing device 114 may generate a first triangle split sub-surface by connecting the inner boundary point a1, the outer boundary point a2, and the inner boundary point b1, sequentially. The processing device 114 may generate a second triangle split sub-surface by connecting the inner boundary point b1 and the outer boundary point b2. Similarly, the processing device 114 may generate a 2nth triangle split sub-surface by connecting the outer boundary point n2 and the inner boundary point a1. Accordingly, the processing device 114 may generate a plurality of triangle split sub-surface by alternately connecting the inner boundary points and the outer boundary points corresponding to the plurality of points. The processing device 114 may combine the plurality of triangle split sub-surface (e.g., the first triangle split sub-surface, the second split sub-surface, . . . , and the 2nth triangle split sub-surface) to generate the split surface. More descriptions of the generation of the split surface may be found elsewhere in the present disclosure (e.g., FIGS. 15A, 15B, and descriptions thereof).

In 1170, the processing device 114 (e.g., the splitting unit 1007) may split the 3D model based on the split surface In some embodiments, the processing device 114 may generate at least two sub-models by splitting the 3D model based on the split surface. In some embodiments, the at least two sub-models may include a desired model, e.g., a 3D orthosis model, as described elsewhere in the present disclosure. In some embodiments, the processing device 114 may split the 3D model based on the split surface according to one or more splitting algorithms. Exemplary splitting algorithms may include a union set algorithm, a difference set algorithm, an intersection algorithm, or the like. In some embodiments, the processing device 114 may call a clip interface in a computational geometry algorithm library (CGAL) to split the 3D model based on the split surface.

In some embodiments, the processing device 114 may render at least one sub-model (e.g., the desired model). In some embodiments, the processing device 114 may transform data associated with the at least one sub-model stored in the surface mesh to a format that can be rendered. For example, the processing device 114 may transform the data associated with the at least one sub-model from a STL format to a polydata format. The processing device 114 may render the at least one sub-model based on the data associated with the at least one sub-model with the polydata format according to one or more rendering algorithms.

The processing device 114 may display the at least one rendered sub-model (e.g., the desired model) on a terminal device (e.g., the terminal device 130) associated with a user. For example, a 3D orthosis model may be displayed on the terminal device 130. The 3D orthosis model may further be modified (e.g., split) by comparing the 3D orthosis model with one or more reference images of a subject. As another example, the 3D orthosis model may be transmitted to a 3D printer for printing.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted. For example, operation 1110 may be omitted. In some embodiments, one or more operations may be performed simultaneously. For example, operations 1130 and 1140 may be performed simultaneously.

Figure 12:
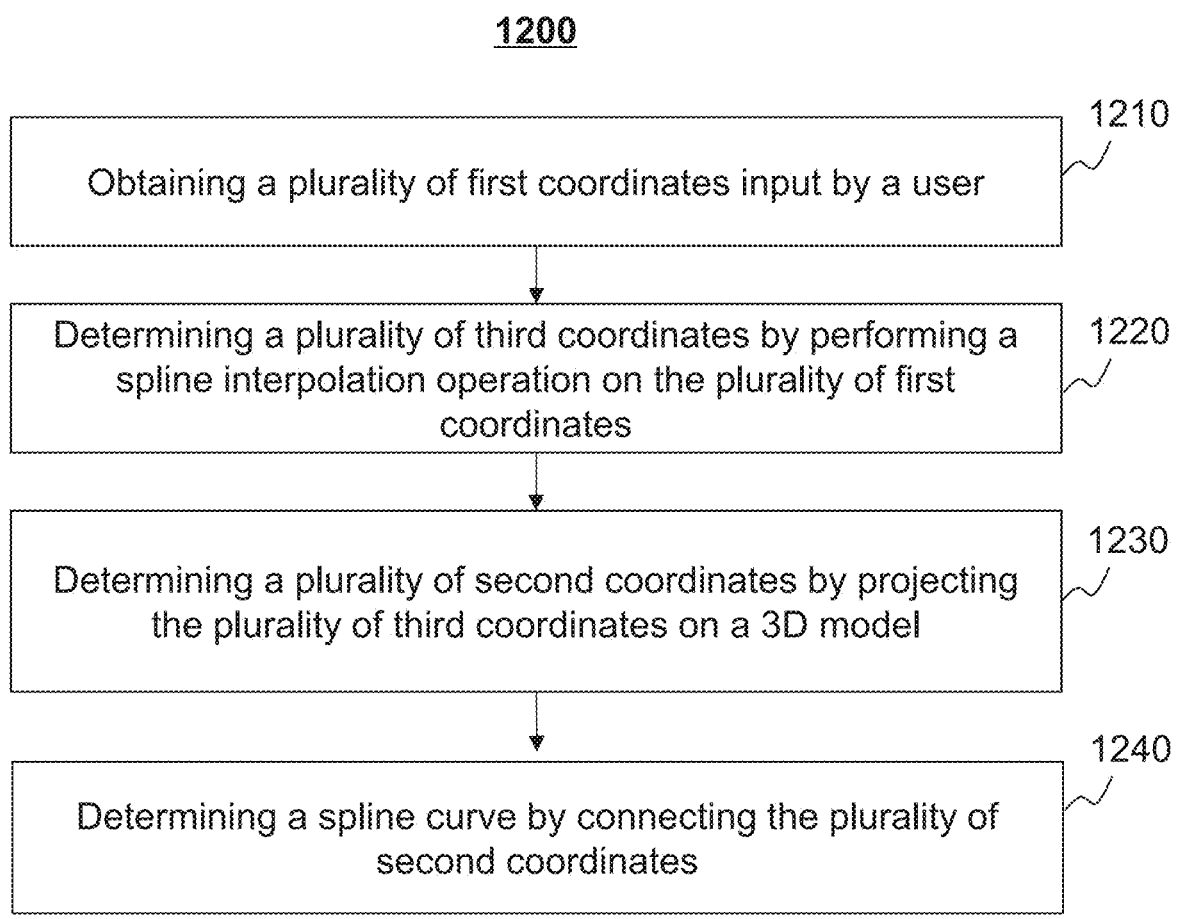
FIG. 12 is a flowchart illustrating an exemplary process for determining a spline curve according to some embodiments of the present disclosure.

FIG. 12 is a flowchart illustrating an exemplary process for determining a spline curve according to some embodiments of the present disclosure. Process 1200 may be executed by the orthosis design system 100. For example, process 1200 may be implemented as a set of instructions (e.g., an application) stored in the storage device 150 in the orthosis design system 100. The processing device 114 may execute the set of instructions and may accordingly be directed to perform process 1200 in the orthosis design system 100. The operations of the illustrated process 1200 presented below are intended to be illustrative. In some embodiments, process 1200 may be accomplished with one or more additional operations not described, and/or without one or more of the operations discussed. Additionally, the order in which the operations of process 1200 as illustrated in FIG. 12 and described below is not intended to be limiting.

In 1210, the processing device 114 (e.g., the spline curve determination unit 1002) may obtain a plurality of first coordinates input by a user.

In some embodiments, the processing device 114 may obtain the plurality of first coordinates in real time or periodically (e.g., per 0.1 seconds, pre 0.5 seconds). In some embodiments, the user may input the plurality of first coordinates via a terminal device (e.g., the terminal device 130). For example, the user may select (e.g., click) a plurality of points on a 3D model displayed on a screen of a terminal device (e.g., the terminal device 130) via a mouse or a finger. In some embodiments, the user may select the plurality of points on the 3D model while rotating the 3D model. The processing device 114 may obtain a plurality of screen coordinates (e.g., the plurality of first coordinates) corresponding to the plurality of selected points in a screen coordinate system. In some embodiments, the processing device 114 may transform the plurality of screen coordinates of the plurality of selected points to a plurality of view coordinates in a view coordinate system. The processing device 114 may store the plurality of view coordinates in a storage device (e.g., the storage device 150) of the orthosis design system 100, or an external storage device for further processing. More descriptions of the coordinate transformations may be found elsewhere in the present disclosure (e.g., FIG. 13 and descriptions thereof).

In 1220, the processing device 114 (e.g., the spline curve determination unit 1002) may determine a plurality of third coordinates by performing a spline interpolation operation on the plurality of first coordinates.

As used herein, spline interpolation may refer to a form of interpolation where the interpolant is a special type of piecewise polynomial called a spline. Exemplary spline interpolation operations may include a cubic B-spline interpolation, a Bezier curve interpolation, a catmull-rom curve interpolation, or the like.

In the present disclosure, each third coordinate may correspond to an interpolation point, and the plurality of third coordinates may correspond to a plurality of interpolation points. For example, in the screen coordinate system, a position of an interpolation point may be represented by an X-axis coordinate and a Y-axis coordinate. The X-axis coordinate and the Y-axis coordinate of the interpolation point may be referred to as a third coordinate of the interpolation point.

In some embodiments, the processing device 114 may perform the spline interpolation operation on the plurality of first coordinates after the plurality of first coordinates are all input by the user. In some embodiments, the processing device 114 may perform the spline interpolation operation on the plurality of first coordinates in real time. For example, a user may input a plurality of input points, e.g., a first input point, a second input point, a third input point, . . . , and a nth input point, via a terminal device (e.g., the terminal device 130) sequentially. After the second input point is input by the user, the processing device 114 may perform the spline interpolation operation on the first input point and the second input point, to determine a first group of interpolation points. After the third input point is input by the user, the processing device 114 may perform the spline interpolation operation on the second input point and the third input point, to determine a second group of interpolation points. Similarly, after the nth input point is input by the user, the processing device 114 may perform the spline operation on the (n−1)th input point and the nth input point, to determine a (n−1)th group of interpolation points. The processing device 114 may perform the spline operation on the nth input point and the first input point, to determine a nth group of interpolation points. In some embodiments, the processing device 114 may determine a plurality of screen coordinates of the plurality of groups of the interpolation points (e.g., the first group of interpolation points, the second group of interpolation points, . . . , the nth group of interpolation points) as the plurality of third coordinates. In some embodiments, the processing device 114 may determine a plurality of screen coordinates of the plurality of groups of the interpolation points (e.g., the first group of interpolation points, the second group of interpolation points, . . . , the nth group of interpolation points) and the plurality of input points, as the plurality of third coordinates.

In 1230, the processing device 114 (e.g., the spline curve determination unit 1002) may determine the plurality of second coordinates by projecting the plurality of third coordinates on a 3D model.

In some embodiments, the processing device 114 may determine the plurality of second coordinates based on the plurality of third coordinates according to one or more coordinate transformation operations. For example, the processing device 114 may transform the plurality of third coordinates in the screen coordinate system to a plurality of fourth coordinates in a view coordinate system. The processing device 114 may transform the plurality of fourth coordinates in the view coordinate system to a plurality of fifth coordinates in a camera coordinate system. The processing device 114 may transform the plurality of fifth coordinates in the camera coordinate system to a plurality of sixth coordinates in the world coordinate system. The processing device 114 may transform the plurality of sixth coordinates in the world coordinate system to the plurality of second coordinates in the model coordinate system. More descriptions of the coordinate transformation operations may be found elsewhere in the present disclosure (e.g., FIG. 13, and descriptions thereof).

In 1240, the processing device 114 (e.g., the spline curve determination unit 1002) may determine a spline curve by connecting the plurality of second coordinates.

In some embodiments, the plurality of second coordinates may be connected manually by a user (e.g., an orthosis designer). For example, a user may draw a line passing through the plurality of second coordinates on the 3D model displayed on the screen of the terminal device 130 to generate the spline curve. In some embodiments, the plurality of second coordinates may be connected automatically by one or more components (e.g., the processing device 114) of the orthosis design system 100. For example, the processing device 114 may connect the plurality of second coordinates by using a CATScript program. Specifically, the plurality of second coordinates may be transformed into a plurality of coordinate scripts via the CATScript program. The spline curve may be generated based on the plurality of coordinate scripts.

According to some embodiments of the present disclosure, by performing the spline interpolation operation on the plurality of first coordinates input by the user, the plurality of third coordinates may be determined. The plurality of second coordinates may be determined by projecting the plurality of third coordinates on the 3D model, and accordingly a relatively smooth spline curve may be generated based on the plurality of second coordinates.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 13:
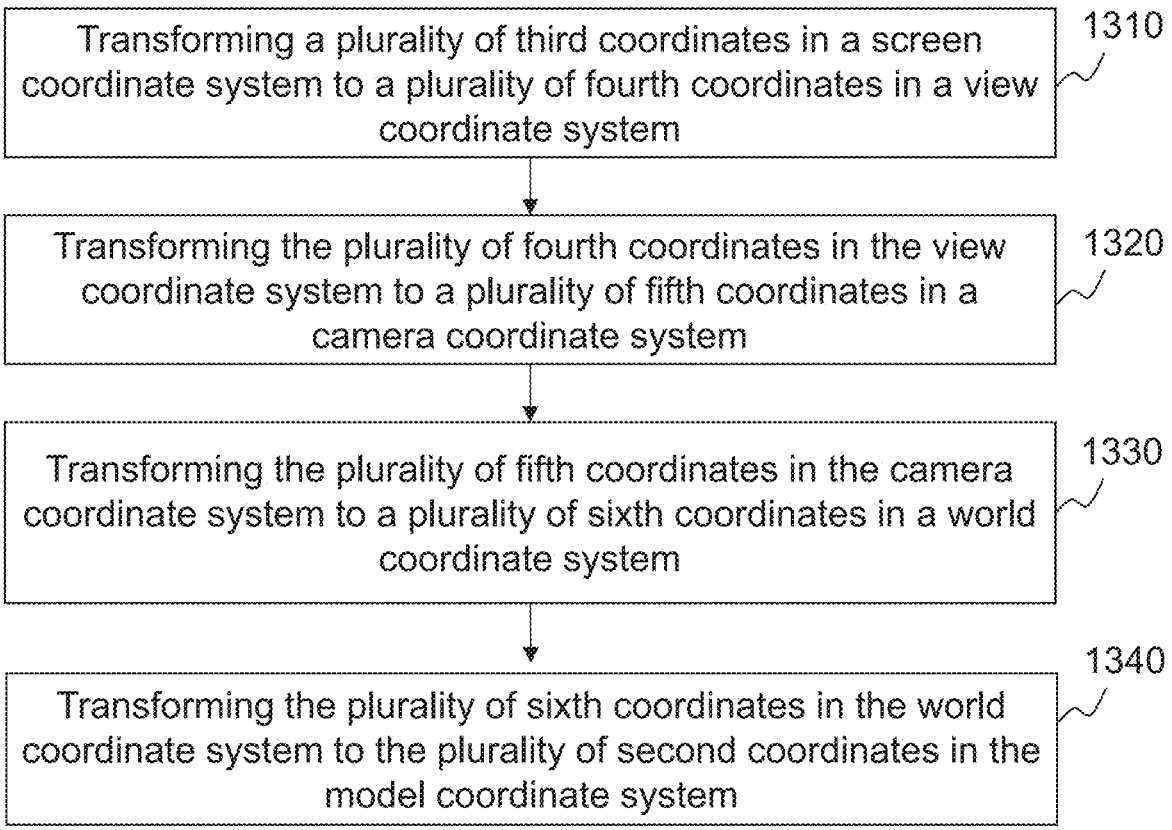
FIG. 13 is a flowchart illustrating an exemplary process for determining a plurality of second coordinates on a spline curve according to some embodiments of the present disclosure.

FIG. 13 is a flowchart illustrating an exemplary process for determining a plurality of second coordinates on a spline curve according to some embodiments of the present disclosure. Process 1300 may be executed by the orthosis design system 100. For example, process 1300 may be implemented as a set of instructions (e.g., an application) stored in the storage device 150 in the orthosis design system 100. The processing device 114 may execute the set of instructions and may accordingly be directed to perform process 1300 in the orthosis design system 100. The operations of the illustrated process 1300 presented below are intended to be illustrative. In some embodiments, process 1300 may be accomplished with one or more additional operations not described, and/or without one or more of the operations discussed. Additionally, the order in which the operations of process 1300 as illustrated in FIG. 13 and described below is not intended to be limiting.

In 1310, the processing device 114 (e.g., the spline curve determination unit 1002) may transform a plurality of third coordinates in a screen coordinate system to a plurality of fourth coordinates in a view coordinate system.

The view coordinate system may refer to a coordinate system for observing a 3D object at different distances and angles. The view coordinate system may be a three-dimensional coordinate system. The view coordinate system may describe a 3D object (e.g., a 3D model) with respect to a viewer (e.g., a camera), and may be defined by a viewpoint of the viewer.

In some embodiments, the processing device 114 may transform the plurality third coordinates (e.g., a plurality of screen coordinates) to the plurality of fourth coordinates (e.g., a plurality of view coordinates) based on depth information associated with the plurality of third coordinates. As used herein, the depth information associated with a point may reflect a Z-axis value of the point in the screen coordinate system. The Z-axis of the screen coordinate system may point out of the screen or into the screen. In some embodiments, the depth information may be determined using an open graphics library (OpenGL). For example, the depth information associated with screen coordinates may be determined using a glReadPixels function in the OpenGL. As used herein, OpenGL may refer to a cross-language, cross-platform application programming interface (API) for rendering 2D and 3D vector graphics.

In 1320, the processing device 114 (e.g., the spline curve determination unit 1002) may transform the plurality of fourth coordinates in the view coordinate system to a plurality of fifth coordinates in a camera coordinate system In some embodiments, the processing device 114 may transform the plurality of fourth coordinates (e.g., the plurality of view coordinates) to the plurality of fifth coordinates (e.g., a plurality of camera coordinates) based on a projection matrix. For example, the processing device 114 may determine the plurality of fifth coordinates by multiplying the plurality of fourth coordinates with the projection matrix.

In some embodiments, the projection matrix may be related to a plurality of parameters (e.g., a plurality of intrinsic parameters) of a camera. For example, the plurality of intrinsic parameters of the camera may form the projection matrix. The projection matrix may be used to perform a transformation between view coordinates denoted by the view coordinate system and camera coordinates denoted by the camera coordinate system.

In some embodiments, the projection matrix may be manually set by a user of the orthosis design system 100, or determined by one or more components (e.g., the processing device 114) of the orthosis design system 100. In some embodiments, the projection matrix may be stored in one or more storage devices (e.g., the storage device 150) of the orthosis design system 100. The processing device 114 may access the one or more storage devices and retrieve the projection matrix.

In 1330, the processing device 114 (e.g., the spline curve determination unit 1002) may transform the plurality of fifth coordinates in the camera coordinate system to a plurality of sixth coordinates in a world coordinate system.

In some embodiments, the processing device 114 may transform the plurality of fifth coordinates (e.g., the plurality of camera coordinates) to the plurality of sixth coordinates (e.g., a plurality of world coordinates) based on a view matrix. For example, the processing device 114 may determine the plurality of sixth coordinates by multiplying the plurality of fifth coordinates with the view matrix.

In some embodiments, the view matrix may be related to a plurality of parameters (e.g., a plurality of extrinsic parameters) of the camera. For example, the plurality of extrinsic parameters of the camera may form the view matrix. The view matrix may be used to perform a transformation between world coordinates denoted by the world coordinate system and camera coordinates denoted by the camera coordinate system.

In some embodiments, the view matrix may be manually set by a user of the orthosis design system 100, or determined by one or more components (e.g., the processing device 114) of the orthosis design system 100. In some embodiments, the view matrix may be stored in one or more storage devices (e.g., the storage device 150) of the orthosis design system 100. The processing device 114 may access the one or more storage devices and retrieve the view matrix.

In 1340, the processing device 114 (e.g., the spline curve determination unit 1002) may transform the plurality of sixth coordinates in the world coordinate system to the plurality of second coordinates in the model coordinate system.

In some embodiments, the processing device 114 may transform the plurality of sixth coordinates (e.g., the plurality of world coordinates) to the plurality of second coordinates (e.g., a plurality of model coordinates) based on a model matrix. The model matrix may be a transformation matrix that translates, scales and/or rotates a 3D model to place it in a world space at a location/orientation it belongs to. For example, the processing device 114 may determine the plurality of second coordinates by multiplying the plurality of sixth coordinates with an inverse of the model matrix.

In some embodiments, the model matrix may be manually set by a user of the orthosis design system 100, or determined by one or more components (e.g., the processing device 114) of the orthosis design system 100. In some embodiments, the model matrix may be stored in one or more storage devices (e.g., the storage device 150) of the orthosis design system 100. The processing device 114 may access the one or more storage devices and retrieve the model matrix.

In some embodiments, the processing device 114 may perform a ray casting operation on the plurality of second coordinates according to a ray casting algorithm. As used herein, ray casting may be the use of ray-surface intersection tests to solve a variety of problems in 3D computer graphics and computational geometry. The ray casting may be a computer graphics rendering algorithm that use the geometric algorithm of ray tracing. Ray tracing-based rendering algorithms may operate in image order to render 3D scenes to 2D images.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, model coordinates may be transformed to screen coordinates. In some embodiments, the model coordinates in the model coordinate system may be transformed to world coordinates based on the model matrix. For example, the world coordinates may be determined by multiplying the model coordinates with the model matrix. The world coordinates may be transformed to camera coordinates based on the view matrix. For example, the camera coordinates may be determined by multiplying the world coordinates with an inverse of the view matrix. The camera coordinates may be transformed to view coordinates based on the projection matrix. For example, the view coordinates may be determined by multiplying the camera coordinates with an inverse of the projection matrix. The view coordinates may be transformed to the screen coordinate by performing a viewport transformation operation on the view coordinates. As used herein, a viewport transformation may refer to a process of mapping view coordinates to screen coordinates where each coordinate corresponds to a point on a screen. For example, the view coordinates may be transformed to screen coordinates by performing the viewport transformation operation on the view coordinates using the OpenGL.

FIG. 14 is a schematic diagram illustrating an exemplary process for determining a center point according to some embodiments of the present disclosure.

As illustrated in FIG. 14, 1401 refers to a 3D model of a human body. The 3D model 1401 may be positioned in a model coordinate system. An origin (not shown in FIG. 14) of the model coordinate system may be a center point of the 3D model 1401. A positive X axis direction (not shown in FIG. 14) may be from a right side to a left side of the 3D model 1401 viewed from the direction facing the front of the 3D model 1401. A positive Y axis direction (not shown in FIG. 14) may be from a front side to a rear side of the 3D model 1401. A positive Z axis direction may be from an upper side to a lower side of the 3D model 1401.

As illustrated in FIG. 14, 1402 refers to a spline curve associated with the 3D model 1401. The spline curve 1401 includes a plurality of points, e.g., a first point P1, a second point P2, and a third point P3. The processing device 114 may project the first point P1 on the Z-axis of the model coordinate system, to generate a first center point C1 corresponding to the first point P1. The processing device 114 may determine a first link line L1 connecting the first point P1 and the first center point C1. The processing device 114 may project the second point P2 on the Z-axis of the model coordinate system, to generate a second center point C2 corresponding to the second point P2. The processing device 114 may determine a second link line L2 connecting the second point P2 and the second center point C2. The processing device 114 may project the third point P3 on the Z-axis of the model coordinate system, to generate a third center point C3 corresponding to the third point P3. The processing device 114 may determine a third link line L3 connecting the third point P3 and the third center point C3.

FIG. 15A is a schematic diagram illustrating an exemplary split surface according to some embodiments of the present disclosure. FIG. 15B is an enlarged view of the region A shown in FIG. 15A according to some embodiments of the present disclosure.

As illustrated in FIG. 15A, 1501 refers to a split surface. The split surface includes a plurality of triangle split sub-surface. The plurality of triangle split sub-surface may be determined based on a plurality of inner boundary points and a plurality of outer boundary points corresponding to a plurality of points on a spline curve (not shown in FIGS. 15A and 15B).

As shown in FIG. 15B, a1 and a2 refer to an inner boundary point and an outer boundary point for a first point (not shown in FIGS. 15A and 15B) on the split curve, respectively, b1 and b2 refer to an inner boundary point and an outer boundary point for a second point (not shown in FIGS. 15A and 15B) on the split curve, respectively, c1 and c2 refer to an inner boundary point and an outer boundary point for a third point (not shown in FIGS. 15A and 15B) on the split curve. The processing device 114 may generate a first triangle split sub-surface s1 by connecting the inner boundary point a1, the outer boundary point a2, and the inner boundary point b1, sequentially. The processing device 114 may generate a second triangle split sub-surface s2 by connecting the inner boundary point b1 and the outer boundary point b2. The processing device 114 may generate a third triangle split sub-surface by connecting the outer boundary point b2 and the inner boundary point c1. The processing device 114 may generate a fourth triangle split sub-surface by connecting the inner boundary point c1 and the outer boundary point c2. Similarly, the processing device 114 may generate the plurality of triangle split sub-surface by alternately connecting the plurality inner boundary points and the plurality of outer boundary points corresponding to the plurality of points on the spline curve. The processing device 114 may combine the plurality of triangle split sub-surface (e.g., the first triangle split sub-surface s1, the second split sub-surface s2, the third split sub-surface s3, the fourth split sub-surface s4) to generate the split surface 1501.

Figure 16:
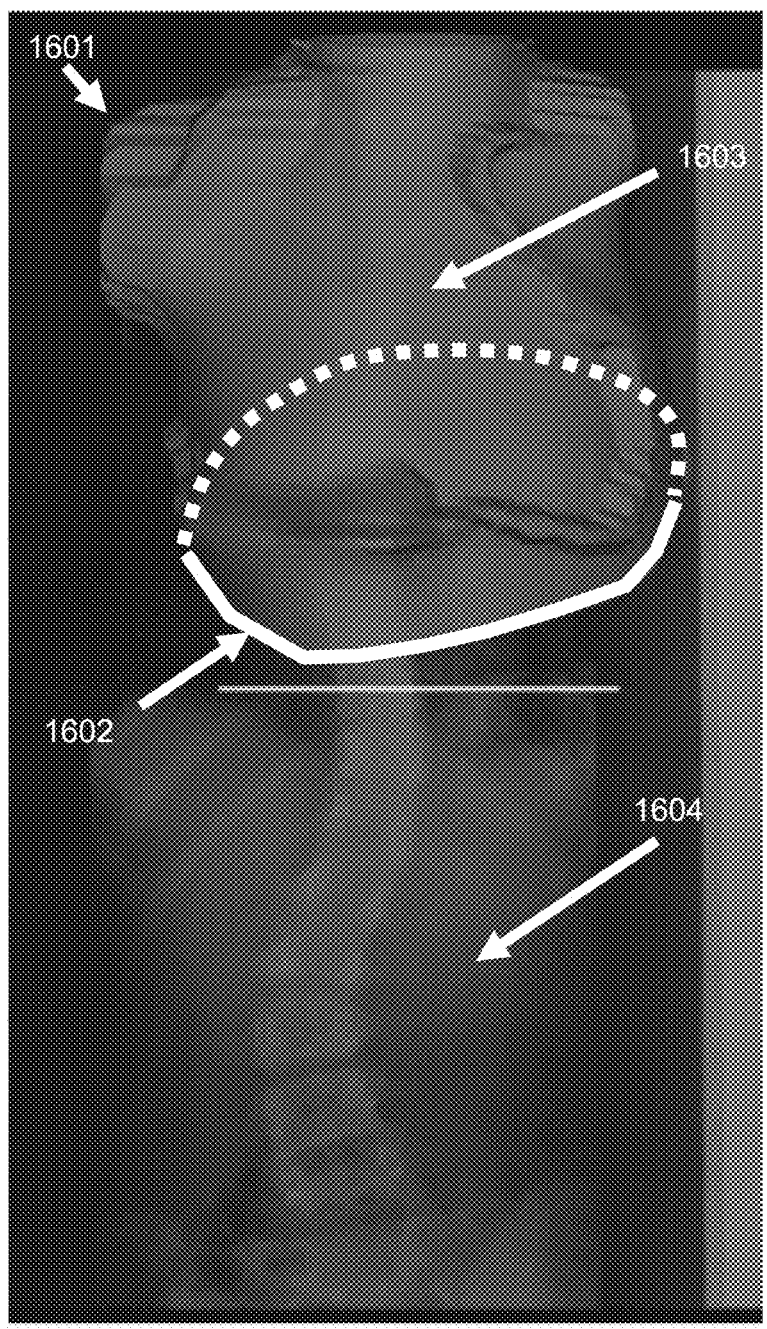
FIG. 16 is a schematic diagram illustrating exemplary 3D sub-models according to some embodiments of the present disclosure.

FIG. 16 is a schematic diagram illustrating exemplary 3D sub-models according to some embodiments of the present disclosure.

As illustrated in FIG. 16, 1602 refers to a split surface of a 3D model 1601. The 3D model 1601 may be split into two 3D sub-models (e.g., a 3D sub-model 1603 and a 3D sub-model 1604) based on the split surface 1602. In some embodiments, the 3D sub-model 1604 may be deleted, and the 3D sub-model may be displayed on an interface of a terminal device of a user.

FIG. 17 is a block diagram illustrating an exemplary data management system according to some embodiments of the present disclosure. In some embodiments, a data management system 1700 may include an importing module 1701, a storage module 1702, and a printing module 1703. The modules may be hardware circuits of at least part of the data management system 1700. The modules may also be implemented as an application or set of instructions read and executed by the data management system 1700. Further, the modules may be any combination of the hardware circuits and the application/instructions. For example, the modules may be part of the data management system 1700 when the data management system 1700 is executing the application or set of instructions. In some embodiments, the data management system 1700 may be part of the orthosis design system 100.

The data management system 1700 may be configured to manage data associated with the orthosis design system 100. The data associated with the orthosis design system 100 may include identification information of the subject (e.g., an identification (ID) number of the subject, a name of the subject, the gender of the subject, the age of the subject, a portion of the subject to be corrected), image data of the subject, a 3D model of the subject, orthosis design data, housing design data associated with a housing of the orthosis, a 3D printing parameter of the orthosis, or the like, or any combination thereof.

The importing module 1701 may be configured to import data associated with the orthosis design system 100. In some embodiments, the importing module 1701 may import data associated with a subject from a local database. In some embodiments, the importing module 1701 may import data associated with a subject from a web database. In some embodiments, the importing module 1701 may generate a patient list for a subject. In some embodiments, the importing module 1701 may be a first terminal device associated with a first type of user (e.g., a doctor) in the orthosis design system 100.

The storage module 1702 may be configured to store data associated with the orthosis design system 100. In some embodiments, the storage module 1702 may serialize data associated with an orthosis in an orthosis design process. In some embodiments, the storage module 1702 may store the serialized data associated with the orthosis in a local database. In some embodiments, the storage module 1702 may store the serialized data associated with the orthosis in a web database. In some embodiments, the storage module 1702 may be a second terminal device associated with a second type of user (e.g., an orthosis designer) in the orthosis design system 100.

The printing module 1703 may be configured to print an orthosis. In some embodiments, the printing module 1703 may obtain data associated with an orthosis. In some embodiments, the printing module 1703 may obtain a plurality of 3D printing parameters associated with an orthosis. In some embodiments, the printing module 1703 may transmit design data associated with an orthosis and/or a plurality of 3D print parameters associated with the orthosis to a 3D print database. In some embodiments, the printing module 1703 may be a third terminal device associated with a third type of user (e.g., a 3D print manufacturer) in the orthosis design system 100.

It should be noted that the above description of the data management system 1700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be added or omitted in the data management system 1700. For example, the printing module 1703 may be omitted. The orthosis design system 100 may include a 3D printing device. The 3D printing device may print the orthosis based on data associated with the orthosis and/or a plurality of 3D printing parameters associated with the orthosis.

Figure 18:
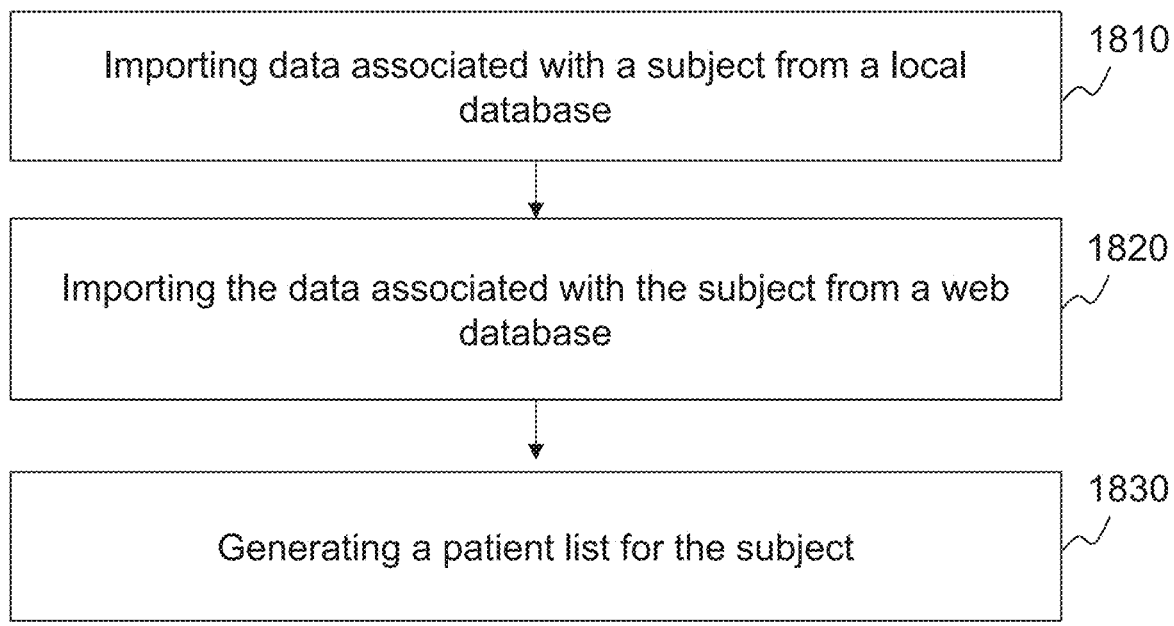
FIG. 18 is a flowchart illustrating an exemplary process for importing data associated with a subject according to some embodiments of the present disclosure.

FIG. 18 is a flowchart illustrating an exemplary process for importing data associated with a subject according to some embodiments of the present disclosure. The process 1800 may be executed by the importing module 1701 of the data management system 1700. For example, process 1800 may be implemented as a set of instructions stored in a storage device in the data management system 1700. The importing module 1701 may execute the set of instructions and accordingly be directed to perform the process 1800 in the data management system 1700. The operations of the illustrated process 1800 presented below are intended to be illustrative. In some embodiments, the process 1800 may be accomplished with one or more additional operations not described, and/or without one or more of the operations discussed. Additionally, the order in which the operations of the process 1800 as illustrated in FIG. 18 and described below is not intended to be limiting.

In 1810, the importing module 1701 may import data associated with a subject from a local database.

In some embodiments, the data associated with the subject an identification (ID) number of the subject, a name of the subject, the gender of the subject, the age of the subject, an address of the subject, a phone number of the subject, a height of the subject, a weight of the subject, a portion of the subject to be corrected, image data associated with the subject, a 3D model associated with the subject, a reference image associated with the subject, a description of medical service or medication that is supplied to the subject (e.g., an examination date, a scan date), or the like, or any combination thereof.

In some embodiments, the importing module 1701 may import the data associated with the subject from one or more components (e.g., the terminal device 130) of the orthosis design system 100. For example, the terminal device 130 may obtain image data associated with the subject from the data obtaining device 110 via the network 120. The importing module 1701 may import the image data associated with the subject from the terminal device 130.

In 1820, the importing module 1701 may import the data associated with the subject from a web database.

In some embodiments, the importing module 1701 may import the data associated with the subject from the web database via the network 120. For example, the data associated with the subject may be serialized. The serialized data associated with the subject may be transmitted from the web databased to the importing module 1701. The serialized data associated with the subject may be deserialized in the importing module 1701. In some embodiments, the data associated with the subject may be imported in the importing module 1701 in a bookmark mode.

In 1830, the importing module 1701 may generate a patient list for the subject.

As used herein, a patient list may refer to all records, documents, lists, electronic media, or any other method of recordation that shows a person to whom a doctor supplies a medical service. In some embodiments, the patient list may include the data associated with the subject, as illustrated in FIG. 23.

For illustration purposes, a user (e.g., a doctor) may log in the data management system 1700 via a browser on the terminal device 130. The user may generate, edit, modify and/or delete a patient list for a subject in the data management system 1700. For example, the user may import data associated with the subject (e.g., a 3D model, a reference image) from a local database and/or a web database. The user may select and view the data associated with the subject on an interface of the terminal device 130.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 1810 and 1820 may be performed simultaneously. As another example, operation 1820 may be performed before operation 1810.

Figure 19:
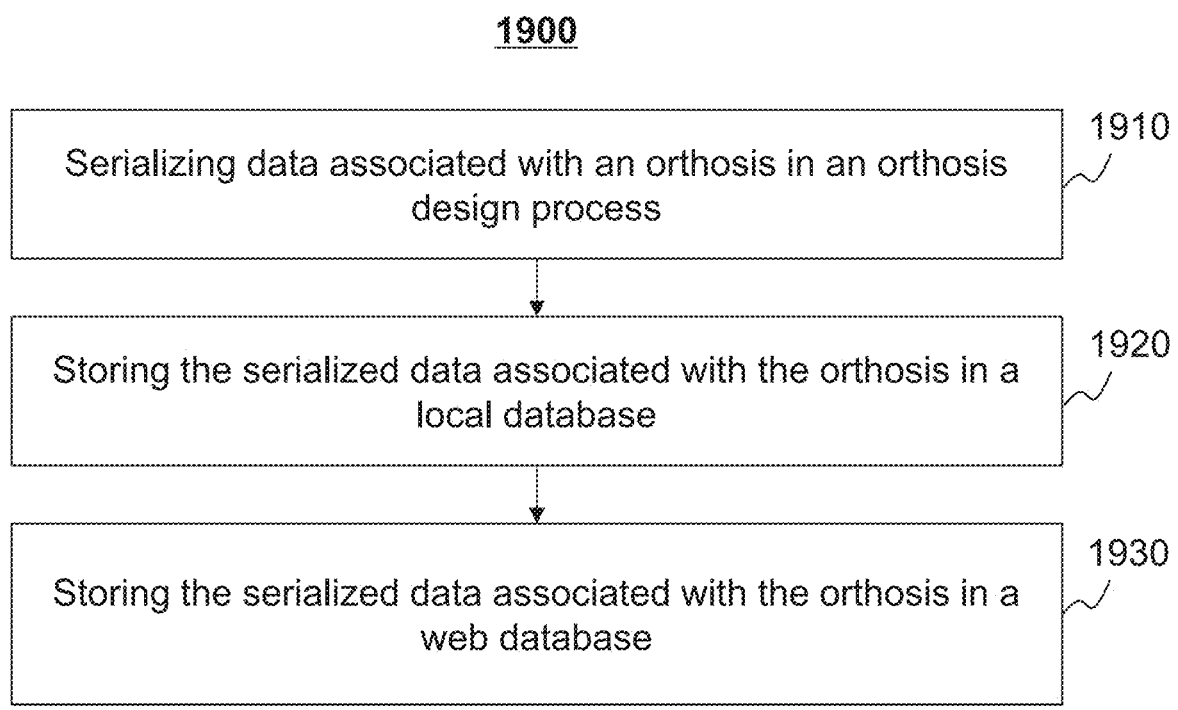
FIG. 19 is a flowchart illustrating an exemplary process for storing data associated with an orthosis according to some embodiments of the present disclosure.

FIG. 19 is a flowchart illustrating an exemplary process for storing data associated with an orthosis according to some embodiments of the present disclosure. The process 1900 may be executed by the storage module 1702 of the data management system 1700. For example, process 1900 may be implemented as a set of instructions stored in a storage device in the data management system 1700. The storage module 1702 may execute the set of instructions and accordingly be directed to perform the process 1900 in the data management system 1700. The operations of the illustrated process 1900 presented below are intended to be illustrative. In some embodiments, the process 1900 may be accomplished with one or more additional operations not described, and/or without one or more of the operations discussed. Additionally, the order in which the operations of the process 1900 as illustrated in FIG. 19 and described below is not intended to be limiting.

In 1910, the storage module 1702 may serialize data associated with an orthosis in an orthosis design process.

As used herein, data serialization may refer to a process of translating data structures or object state into a format that can be stored (e.g., in a file or memory buffer) or transmitted (e.g., across a network connection link) and reconstructed later (e.g., in a different computer environment).

In some embodiments, during the orthosis design process, the data associated with the orthosis may be generated. The data associated with the orthosis may include orthosis design data, housing design data, a spline curve associated with an orthosis model, a split surface of the orthosis model, or the like, or any combination thereof. The storage module 1702 may convert the data associated with the orthosis into a sequence of bytes which can be stored in a database or can be transmitted through the network 120.

In 1920, the storage module 1702 may store the serialized data associated with the orthosis in a local database. In some embodiments, the storage module 1702 may store the serialized data associated with the orthosis in the terminal device 130.

In 1930, the storage module 1702 may store the serialized data associated with the orthosis in a web database. In some embodiments, the storage module 1702 may store the serialized data associated with the orthosis in the web database via the network 120.

In some embodiments, the storage module 1702 may store the serialized data associated with the orthosis in the local database and/or the web database automatically. For example, the storage module 1702 may store the serialized data associated with the orthosis in the local database and/or the web database in real time. As another example, the storage module 1702 may store the serialized data associated with the orthosis in the local database and/or the web database periodically (e.g., per 5 seconds, pre 10 seconds). In some embodiments, the storage module 1702 may store the serialized data associated with the orthosis in the local database and/or the web database in response to a request for storage from a user. For example, when the user presses or clicks a "save" button on an interface of the terminal device 130, the storage module 1702 may store the serialized data associated with the orthosis in the local database and/or the web database.

For illustration purposes, a user (e.g., an orthosis designer) may log in the orthosis design system 100 via a browser on a terminal device (e.g., the terminal device 130). The user may view data associated with a subject (e.g., a patient list) imported by another user (e.g., a doctor) via the browser. The user may design an orthosis model based on the data associated with the subject. In some embodiments, during the orthosis design process, the user may generate, edit, modify and/or delete the data associated with the orthosis in the orthosis design system 100. For example, the user may determine orthosis design data based on a 3D model of a subject and one or more reference images of the subject. The orthosis design data may be stored in the local database and/or the web databased automatically.

In some embodiments, a plurality of users (e.g., a plurality of orthosis designers) may design the orthosis model collaboratively. For example, a first user may determine first orthosis design data associated with a first part of orthosis model via a browser on a first terminal device in the orthosis design system 100. The first orthosis design data associated with the first part of orthosis model may be stored in the local database and/or the web database. A second user may determine second orthosis design data associated with a second part of orthosis model via a browser on a second terminal device in the orthosis design system 100. The second orthosis design data associated with the second part of orthosis model may be stored in the local database and/or the web database. A third user may view the first orthosis design data and the second orthosis design data via a browser on a third terminal device in the orthosis design system 100. The third user may determine a 3D orthosis model based on the first orthosis design data and the second orthosis design data. In some embodiments, the first terminal device may be located in a first location. The second terminal device may be located in a second location. The third terminal device may be located in a third location. The first location, the second location, and the third location may be different form each other.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 1910 and 1920 may be performed simultaneously. As another example, operation 1920 may be performed before operation 1910.

Figure 20:
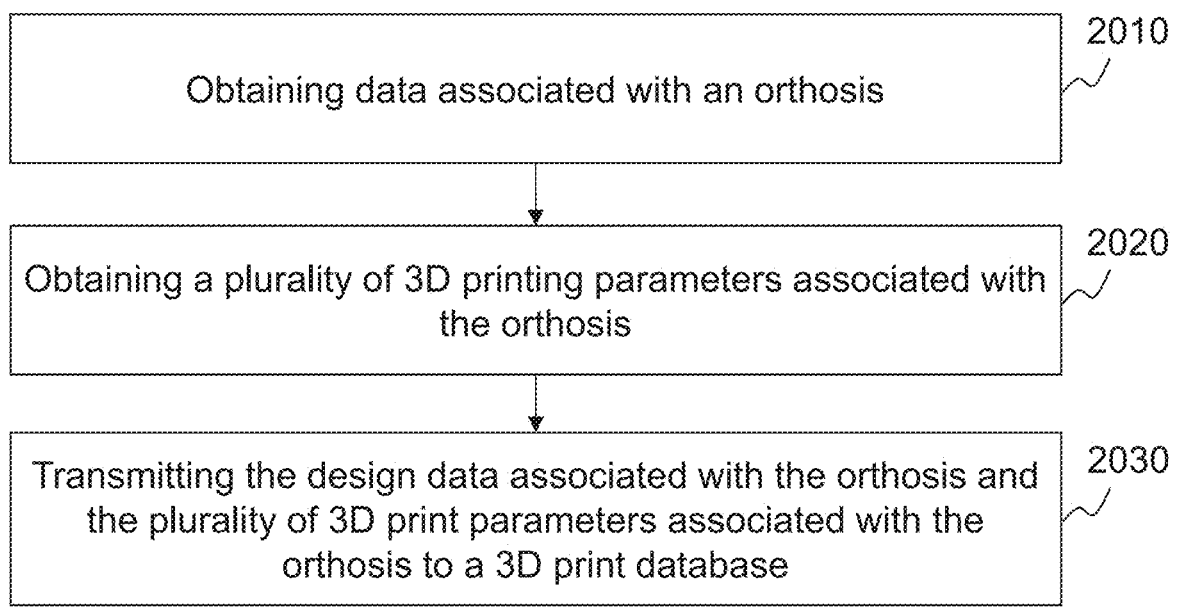
FIG. 20 is a flowchart illustrating an exemplary process for transmitting data to a 3D print database according to some embodiments of the present disclosure.

FIG. 20 is a flowchart illustrating an exemplary process for transmitting data to a 3D print database according to some embodiments of the present disclosure. The process 2000 may be executed by the printing module 1703 of the data management system 1700. For example, process 2000 may be implemented as a set of instructions stored in a storage device in the data management system 1700. The printing module 1703 may execute the set of instructions and accordingly be directed to perform the process 2000 in the data management system 1700. The operations of the illustrated process 2000 presented below are intended to be illustrative. In some embodiments, the process 2000 may be accomplished with one or more additional operations not described, and/or without one or more of the operations discussed. Additionally, the order in which the operations of the process 2000 as illustrated in FIG. 20 and described below is not intended to be limiting.

In 2010, the printing module 1703 may obtain data associated with an orthosis.

In some embodiments, the data associated with the orthosis may include orthosis design data, housing design data, a spline curve associated with an orthosis model, a split surface of the orthosis model, or the like, or any combination thereof. In some embodiments, the printing module 1703 may obtain the data associated with the orthosis from one or more components (e.g., the terminal device 130, the data obtaining device 110, the storage device 150) of the orthosis design system 100 or an external storage device (e.g., a web database) via the network 120. For example, the processing device 114 may transmit the data associated with the orthosis to the storage device 150, or any other storage device for storage. The printing module 1703 may obtain the data associated with the orthosis from the storage device 150, or any other storage device. As another example, the processing device 114 may transmit the data associated with the orthosis to the printing module 1703 directly.

In 2020, the printing module 1703 may obtain a plurality of 3D printing parameters associated with the orthosis.

In some embodiments, the plurality of 3D printing parameters associated with the orthosis may include a printing material, a printing orientation, a layer thickness, a printing orientation angle, a filling ratio, a filament feed rate, or the like, or any combination thereof. In some embodiments, the plurality of 3D printing parameters may be default parameter stored in a storage device (e.g., the storage device 150). In some embodiments, the plurality of 3D printing parameters may be set manually by a user (e.g., an orthosis designer, a doctor) of the orthosis design system 100, or determined by one or more components (e.g., the processing device 114) of the orthosis design system 100 according to different situations. For example, the plurality of 3D printing parameters may be determined based on a portion of the subject to be corrected.

In 2030, the printing module 1703 may transmit the design data associated with the orthosis and the plurality of 3D print parameters associated with the orthosis to a 3D print database.

In some embodiments, the printing module 1703 may transmit the design data associated with the orthosis and the plurality of 3D print parameters associated with the orthosis to a cloud print database of a print manufacturer via the network 120. The print manufacturer may view the design data associated with the orthosis and the plurality of 3D print parameters associated with the orthosis via a browser on a terminal device (e.g., the terminal device 130) in the orthosis design system 100. The print manufacturer may print the orthosis based on the design data associated with the orthosis and the plurality of 3D print parameters associated with the orthosis via a 3D printing device.

Accordingly, a plurality of users (e.g., a doctor, an orthosis designer, a 3D print manufacturer) of the orthosis design system 100 may design and/or print an orthosis for a subject via a plurality of browsers on a plurality of terminal devices (e.g., the plurality of terminal devices 130) collaboratively. The orthosis design and print process may be simplified, and the orthosis production efficiency may be improved.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 2010 and 2020 may be performed simultaneously. As another example, operation 2020 may be performed before operation 2010. As still another example, operation 2030 may be omitted. The printing module 1703 may be a 3D printing device. The 3D printing device may print the orthosis based on the data associated with the orthosis and the plurality of 3D printing parameters associated with the orthosis.

FIG. 21 is a schematic diagram illustrating an exemplary cloud design system according to some embodiments of the present disclosure.

As shown in FIG. 21, a cloud design system 2100 may include a data interaction equipment 140, the server 144, and a file server 145. The data interaction equipment 140 may include a first load balancing device 141, a data interaction device cluster 142, and a second load balancing device 143. The data interaction device cluster 142 may include one or more data interaction devices, e.g., a data interaction device 142-1, a data interaction device 142-2, and a data interaction device 142-3. In some embodiments, the server 144 may be a server group. For example, the server 144 may include a plurality of servers, e.g., a server 144-1, a server 144-2, and a server 144-3. In some embodiments, the terminal device 130 may communicate with the data interaction equipment 140 (e.g., the first load balancing device 141, the data interaction device cluster 142, the second load balancing device 143) via a browser.

The first load balancing device 141 may communicate with the terminal device 130. The first load balancing device 141 may receive data from the terminal device 130, and transmit the received data to at least one data interaction device (e.g., the data interaction device 142-1, the data interaction device 142-2, the data interaction device 142-3) of the data interaction device cluster 142 according to a load balancing mechanism. The data received from the terminal device 130 may include one or more requests for orthosis design. As used herein, load balancing may improve a distribution of workloads across multiple computing resources, such as computers, a computer cluster, network links, central processing units, or disk drives. Load balancing may aim to optimize resource use, maximize throughput, minimize response time, and avoid overload of any single resource.

The data interaction device (e.g., the data interaction device 142-1, the data interaction device 142-2, the data interaction device 142-3) may be configured to determine one or more requests for orthosis design based on the data obtained from the terminal device 130. In some embodiments, the one or more requests for orthosis design may include a medical image of a subject to be corrected, a 3D model of the subject to be corrected, a reference image of the subject to be corrected, a patient ID of the subject to be corrected (e.g., an ID number), a description of the subject to be corrected (e.g., a left tibia, the 3rd to 6th lumbar vertebrae), or the like, or any combination thereof.

The second load balancing device 143 may communicate with the data interaction device cluster 142. The second load balancing device 143 may be configured to transmit the request for orthosis design to the at least one server (e.g., the server 144-1, the server 144-2, and the server 144-3), according to the load balancing mechanism.

The server 144 (e.g., the server 144-1, the server 144-2, and the server 144-3) may communicate with the data obtaining device 110. The server 144 may be configured to perform one or more operations in process 500 to process 700, process 1100 to process 1300, in response to the request for orthosis design. In some embodiments, the server 144 may obtain image data from the data obtaining device 110 based on the request for orthosis design. In some embodiments, the server 144 may obtain image data from the file server 145.

The file server 145 may be configured to store image data obtained by the data obtaining device 110. In some embodiments, the data obtaining device 110 may include a DR device, a 3D camera, a CT device, an MRI device, or the like, as described elsewhere in the present disclosure. In some embodiments, the file server 145 may include a PACS.

For illustration purposes, when a user needs to perform an orthotics design operation, the user may send a request for orthosis design and establish an orthosis design task by accessing the data interaction equipment 140 via a network port (e.g., a browser on a terminal device). The data interaction equipment 140 may receive the request and the orthosis design task, and send the orthosis design task to an orthosis design server (e.g., the server 144). The orthosis design server (e.g., the server 144) may receive an instruction to design the orthosis for a subject. When a plurality of users need to perform the orthotics design operation, the plurality of users may send a plurality of requests for orthosis design and establish a plurality of orthosis design tasks via a plurality of terminal devices (e.g., browsers on the plurality of terminal devices). The data interaction equipment 140 may allocate a network resource load of the orthotics design server (e.g., the server 144-1, the server 144-2, and the server 144-3) according to a pre-set load balancing strategy. Accordingly, a plurality of orthosis design servers (e.g., the server 144-1, the server 144-2, and the server 144-3) may process the plurality of design orthosis tasks for the plurality of terminal devices synchronously. For example, the data interaction equipment 140 may allocate the orthosis design task to an orthosis design server that is idle or has a relatively small amount of tasks, according to an orthosis design server polling mechanism.

According to some embodiments of the present disclosure, orthosis design data may be generated based on reference image(s) and 3D model of the subject. The orthosis design data may be altered based on force data of at least one region of the subject after wearing the orthosis. Therefore, the orthosis generated based on the orthosis design data may meet correction needs of a user. In addition, one or more users may send one or more requests for orthosis design to a data interaction equipment (e.g. the data interaction equipment 140) via browsers on one or more terminal devices (e.g., the terminal device 130). The data interaction equipment may receive the one or more requests send the one or more requests to one or more orthosis design servers (e.g., the server 144). The one or more orthosis design servers may perform one or more operations in an orthosis design process, in response to the one or more requests for orthosis design. Accordingly, the orthosis design process may be simplified, and a collaborative design of the orthosis by a plurality of users associated with a plurality of terminal devices may be achieved.

Figure 22:
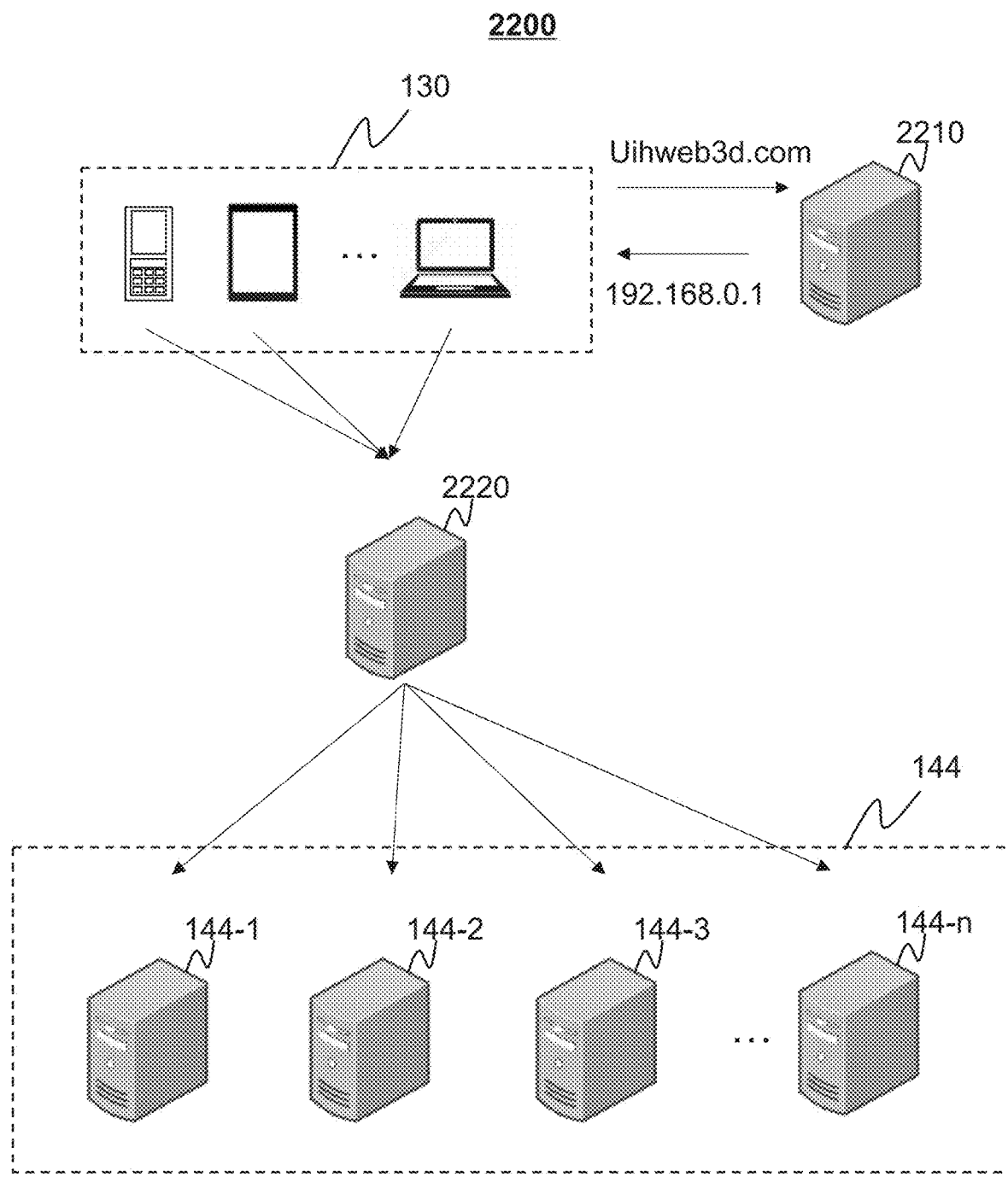
FIG. 22 is a schematic diagram illustrating an exemplary orthosis design system according to some embodiments of the present disclosure.

FIG. 22 is a schematic diagram illustrating an exemplary orthosis design system according to some embodiments of the present disclosure.

As shown in FIG. 22, an orthosis design system 2200 may include a terminal device 130, a server 144, a reverse proxy 2220 (e.g., a nginx), and a DNS server 2210. In some embodiments, the server 144 may be a server group. The server 144 may include a plurality of servers, e.g., a server 144-1, a server 144-2, . . . , and a server 144-n.

The terminal device 130 may be configured to send data (e.g., one or more requests for orthosis design) to the reverse proxy 2220. In some embodiments, the terminal device 130 may communicate with the reverse proxy 2220 via a browser. For example, a user associated with the terminal device 130 may input a domain name in the browser on the terminal device 130. The browser may send the domain name to the DNS server 2210. The DNS server 2210 may translate the domain name into an IP address. For illustration purposes, the DNS server 2210 may translate a domain name "Uihweb3d.com" into an IP address "192.168.0.1", as shown in FIG. 22. The browser may receive the IP address from the DNS server, and transmit the IP address to the reverse proxy 2220.

The reverse proxy 2220 may receive the data (e.g., an IP address) from the terminal device 130, and transmit the data to one or more servers (e.g., the server 144-1, the server 144-2, . . . , the server 144-n) according to a load balancing mechanism. In some embodiments, the reverse proxy 2220 may receive the data from the terminal device 130 via the network 120 (e.g., a public network). The reverse proxy 2220 may transmit the data to the one or more servers via the network 120 (e.g., a local area network).

The server 144 (e.g., the server 144-1, the server 144-2, . . . , the server 144-n) may be configured to perform one or more functions described in the present disclosure. For example, the server group 144 may perform one or more operations in process 500 to process 700, process 1100 to process 1300, in response to a request for orthosis design, and generate processed data. The server 144 may transmit the processed data (e.g., orthosis design data) to the reverse proxy 2220. The reverse proxy 2220 may receive the processed data from the server 144, and transmit the processed data to the terminal device 130. In some embodiments, the reverse proxy 2220 may receive the processed data from the server 144 via the network 120 (e.g., a local area network).

The reverse proxy 2220 may transmit the processed data to the terminal device 130 via the network 120 (e.g., a public network).

In some embodiments, by the using of the reverse proxy, an original IP address of the server 144 may not be revealed. An IP address of the reverse proxy 2220 may only be visible. The security of the orthosis design system 100 may be improved. In some embodiments, the reverse proxy 2220 may expand the server capacity in real time. Accordingly, the orthosis design system 100 may be deployed on a plurality of servers, which may improve the response speed and stability of the orthosis design system in a high concurrency environment. The difficulty of development and maintenance of the orthosis design system 100 may be reduced.

FIG. 23 is a schematic diagram illustrating an exemplary user interface for displaying a patient list according to some embodiments of the present disclosure.

As illustrated, the patient list 2300 may include a personal information section 2301 for displaying personal information associated with a subject. The patient list 2300 may also include a data section 2302 for presenting medical data associated with the subject. The patient list 2300 may further include a function button section 2303 for presenting operations (e.g., "back", "load in") associated with the personal information of the subject and the data of the subject.

Figure 24:
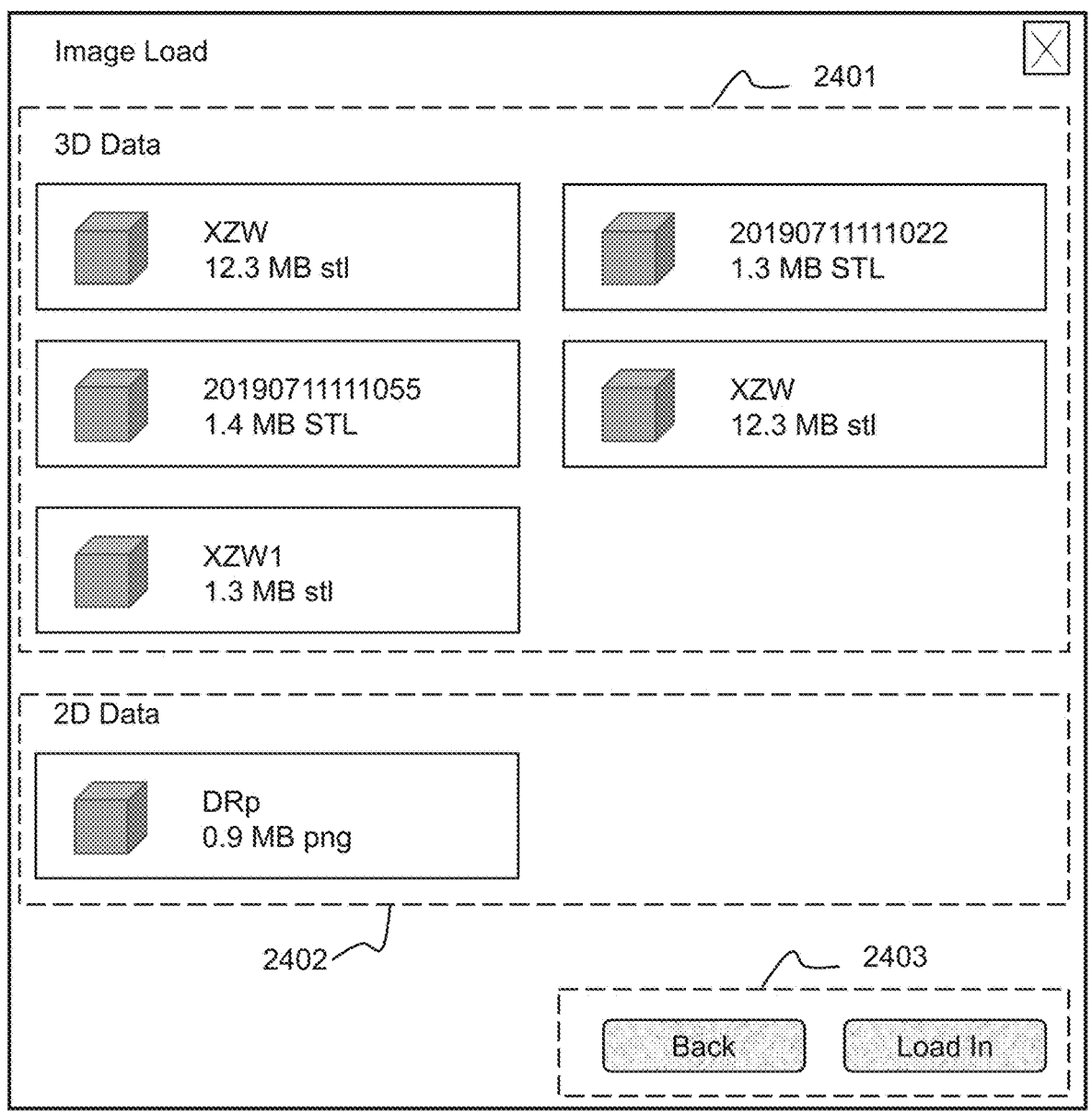
FIG. 24 is a schematic diagram illustrating an exemplary user interface for displaying data associated with a subject in a bookmark mode according to some embodiments of the present disclosure.

FIG. 24 is a schematic diagram illustrating an exemplary user interface for displaying data associated with a subject in a bookmark mode according to some embodiments of the present disclosure.

As illustrated, a user interface 2400 may include a 3D data section for displaying a plurality of 3D data files associated with a subject. The user interface 2400 may include a 2D data section for displaying a plurality of 2D data files associated with the subject. In some embodiments, the plurality of 2D data files and the plurality of 3D data files may be displayed in a bookmark mode. For example, a file name, a file size, a data format, or the like, of a 2D data file or a 3D data file may be displayed. The user interface 2400 may further include a function button section 2403 for presenting operations (e.g., "back", "load in") associated with the data of the subject.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for orthosis design, implemented on a computing device having one or more processors and one or more storage devices, the method comprising:

obtaining a three-dimensional (3D) model associated with a subject;

obtaining one or more reference images associated with the subject;

determining, based on the 3D model and the one or more reference images, orthosis design data for the subject;

simulating, based on the orthosis design data, force data generated by a 3D orthosis model on the 3D model of the subject after wearing the 3D orthosis model; and adjusting the orthosis design data based on the force data and an applied force of the 3D orthosis model on the subject.

2. The method of claim 1, wherein the simulating, based on the orthosis design data, force data generated by a 3D orthosis model on the 3D model of the subject after wearing the 3D orthosis model comprises:

generating the 3D orthosis model based on the orthosis design data;

simulating a curvature degree of at least one mesh of the 3D model of the subject after wearing the 3D orthosis model; and determining the force data based on the curvature degree of the at least one mesh of the 3D model of the subject.

3. The method of claim 1, wherein the applied force of the 3D orthosis model includes a force of a pressure region of an orthosis applied on different regions of the subject during correcting of the subject.

4. The method of claim 1, wherein the adjusting the orthosis design data based on the force data and an applied force of the 3D orthosis model on the subject comprises:

adjusting the orthosis design data based on force magnitudes and force directions of a plurality of meshes of the 3D model of the subject and the applied force of the 3D orthosis model.

5. The method of claim 1, wherein the determining, based on the 3D model and the one or more reference images, orthosis design data for the subject comprises:

superimposing the reference image on the 3D model; and determining the orthosis design data by modifying the 3D model based on a superimposing result.

6. The method of claim 5, wherein the superimposing the reference image on the 3D model comprises:

determining one or more first reference points in the reference image;

determining one or more second reference points corresponding to the one or more first reference points in the 3D model; and superimposing the reference image on the 3D model by aligning the one or more first reference points in the reference image and the one or more corresponding second reference points in the 3D model.

7. The method of claim 5, wherein the determining the orthosis design data by modifying the 3D model based on a superimposing result comprises:

performing a mesh splitting operation on the 3D model.

8. The method of claim 7, wherein the performing a mesh splitting operation on the 3D model comprises:

determining a spline curve associated with the 3D model;

for each point of a plurality of points on the spline curve, determining a center point corresponding to the point;

determining a link line connecting the center point and the corresponding point;

determining a plurality of boundary points along a direction of the link line;

generating a split surface based on boundary points corresponding to the plurality of points on the spline curve;

splitting the 3D model based on the split surface.

9. The method of claim 1, wherein the obtaining one or more reference images associated with the subject comprises:

obtaining identification information of the subject; and obtaining the one or more reference images by inputting the identification information of the subject into an image generation model, wherein the image generation model is trained based on historical image data.

10. The method of claim 1, further comprising:

determining housing design data associated with a housing of an orthosis by performing a thickness-adjustment operation on the orthosis design data, wherein the housing design data represents a size of the orthosis.

11. A system for orthosis design, comprising:

at least one storage medium including a set of instructions; and at least one processor in communication with the at least one storage medium, wherein when executing the set of instructions, the at least one processor is directed to cause the system to perform operations comprising:

obtaining a three-dimensional (3D) model associated with a subject;

obtaining one or more reference images associated with the subject;

determining, based on the 3D model and the one or more reference images, orthosis design data for the subject;

simulating, based on the orthosis design data, force data generated by a 3D orthosis model on the 3D model of the subject after wearing the 3D orthosis model; and adjusting the orthosis design data based on the force data and an applied force of the 3D orthosis model on the subject.

12. The system of claim 11, wherein the simulating, based on the orthosis design data, force data generated by a 3D orthosis model on the 3D model of the subject after wearing the 3D orthosis model comprises:

generating the 3D orthosis model based on the orthosis design data;

simulating a curvature degree of at least one mesh of the 3D model of the subject after wearing the 3D orthosis model; and determining the force data based on the curvature degree of the at least one mesh of the 3D model of the subject.

13. The system of claim 11, wherein the applied force of the 3D orthosis model includes a force of a pressure region of an orthosis applied on different regions of the subject during correcting of the subject.

14. The system of claim 11, wherein the adjusting the orthosis design data based on the force data and an applied force of the 3D orthosis model on the subject comprises:

adjusting the orthosis design data based on force magnitudes and force directions of a plurality of meshes of the 3D model of the subject and the applied force of the 3D orthosis model.

15. The system of claim 11, wherein the determining, based on the 3D model and the one or more reference images, orthosis design data for the subject comprises:

superimposing the reference image on the 3D model; and determining the orthosis design data by modifying the 3D model based on a superimposing result.

16. The system of claim 15, wherein the superimposing the reference image on the 3D model comprises:

determining one or more first reference points in the reference image;

determining one or more second reference points corresponding to the one or more first reference points in the 3D model; and superimposing the reference image on the 3D model by aligning the one or more first reference points in the reference image and the one or more corresponding second reference points in the 3D model.

17. The system of claim 15, wherein the determining the orthosis design data by modifying the 3D model based on a superimposing result comprises:

performing a mesh splitting operation on the 3D model.

18. The system of claim 17, wherein the performing a mesh splitting operation on the 3D model comprises:

determining a spline curve associated with the 3D model;

for each point of a plurality of points on the spline curve,
determining a center point corresponding to the point;
determining a link line connecting the center point and the corresponding point;
determining a plurality of boundary points along a direction of the link line;

generating a split surface based on boundary points corresponding to the plurality of points on the spline curve;

splitting the 3D model based on the split surface.

19. The system of claim 11, wherein the obtaining one or more reference images associated with the subject comprises:

obtaining identification information of the subject; and obtaining the one or more reference images by inputting the identification information of the subject into an image generation model, wherein the image generation model is trained based on historical image data.

20. A non-transitory computer readable medium, comprising executable instructions that, when executed by at least one processor, direct the at least one processor to perform a method for orthosis design, the method comprising:

obtaining a three-dimensional (3D) model associated with a subject;

obtaining one or more reference images associated with the subject;

determining, based on the 3D model and the one or more reference images, orthosis design data for the subject;

simulating, based on the orthosis design data, force data generated by a 3D orthosis model on the 3D model of the subject after wearing the 3D orthosis model; and adjusting the orthosis design data based on the force data and an applied force of the 3D orthosis model on the subject.

* * * * *